United States Patent [19]

Mizukawa et al.

[11] Patent Number: 5,628,771
[45] Date of Patent: May 13, 1997

[54] ELECTROMAGNETIC-WAVE THERMATOLOGICAL DEVICE

[75] Inventors: Satoshi Mizukawa; Shinji Hatta; Nobuyuki Furukawa; Toru Nagase, all of Tokyo, Japan

[73] Assignee: Olympus Optical Co., Ltd., Tokyo, Japan

[21] Appl. No.: 630,556

[22] Filed: Apr. 10, 1996

Related U.S. Application Data

[63] Continuation of Ser. No. 241,298, May 11, 1994, abandoned.

[30] Foreign Application Priority Data

May 12, 1993 [JP] Japan ................. 5-110294
May 12, 1993 [JP] Japan ................. 5-110653

[51] Int. Cl.$^6$ ................................. A61B 17/36
[52] U.S. Cl. ................... 607/102; 607/101; 607/156; 606/31; 606/33; 606/42
[58] Field of Search ................. 606/27–35, 37–42, 606/48–50; 607/100–102, 115, 116, 154–156

[56] References Cited

U.S. PATENT DOCUMENTS

| 4,311,154 | 1/1982 | Sterzer et al. ............ 607/102 |
| 4,375,220 | 3/1983 | Matvias ..................... 607/102 |
| 4,860,752 | 8/1989 | Turner ....................... 607/102 |
| 4,920,978 | 5/1990 | Colvin ....................... 607/102 |
| 4,967,765 | 11/1990 | Turner et al. . |
| 5,234,004 | 8/1993 | Hascoet et al. . |
| 5,413,588 | 5/1995 | Rudie et al. ............... 607/102 |
| 5,433,740 | 7/1995 | Yamaguchi ................. 607/102 |
| 5,456,682 | 10/1995 | Edwards et al. ............ 606/31 |

FOREIGN PATENT DOCUMENTS

| 0485323 | 5/1992 | European Pat. Off. . |
| 0485323A1 | 5/1992 | European Pat. Off. . |
| 63-182759 | 11/1988 | Japan . |
| 2-41976 | 9/1990 | Japan . |

*Primary Examiner*—Angela D. Sykes
*Assistant Examiner*—Michael Peffley
*Attorney, Agent, or Firm*—Frishauf, Holtz, Goodman, Langer & Chick

[57] ABSTRACT

A thermatological device comprising an applicator and a main body. The applicator has a microwave-applying section, a first temperature sensor and a second temperature sensor. The main body contains a control unit. The microwave-applying section applies microwaves to an affected part, thereby treating the part. The first temperature sensor detects the temperature of the affected part being treated. The, the second temperature sensor detects a part located adjacent to the affected part. The control unit controls the microwave-applying section to render the temperature detected by the first temperature sensor equal to a preset target temperature. The control unit causes the microwave-applying section to stop or reduce the emission of microwaves when the temperature detected by the second temperature sensor reaches a preset burn temperature.

9 Claims, 22 Drawing Sheets

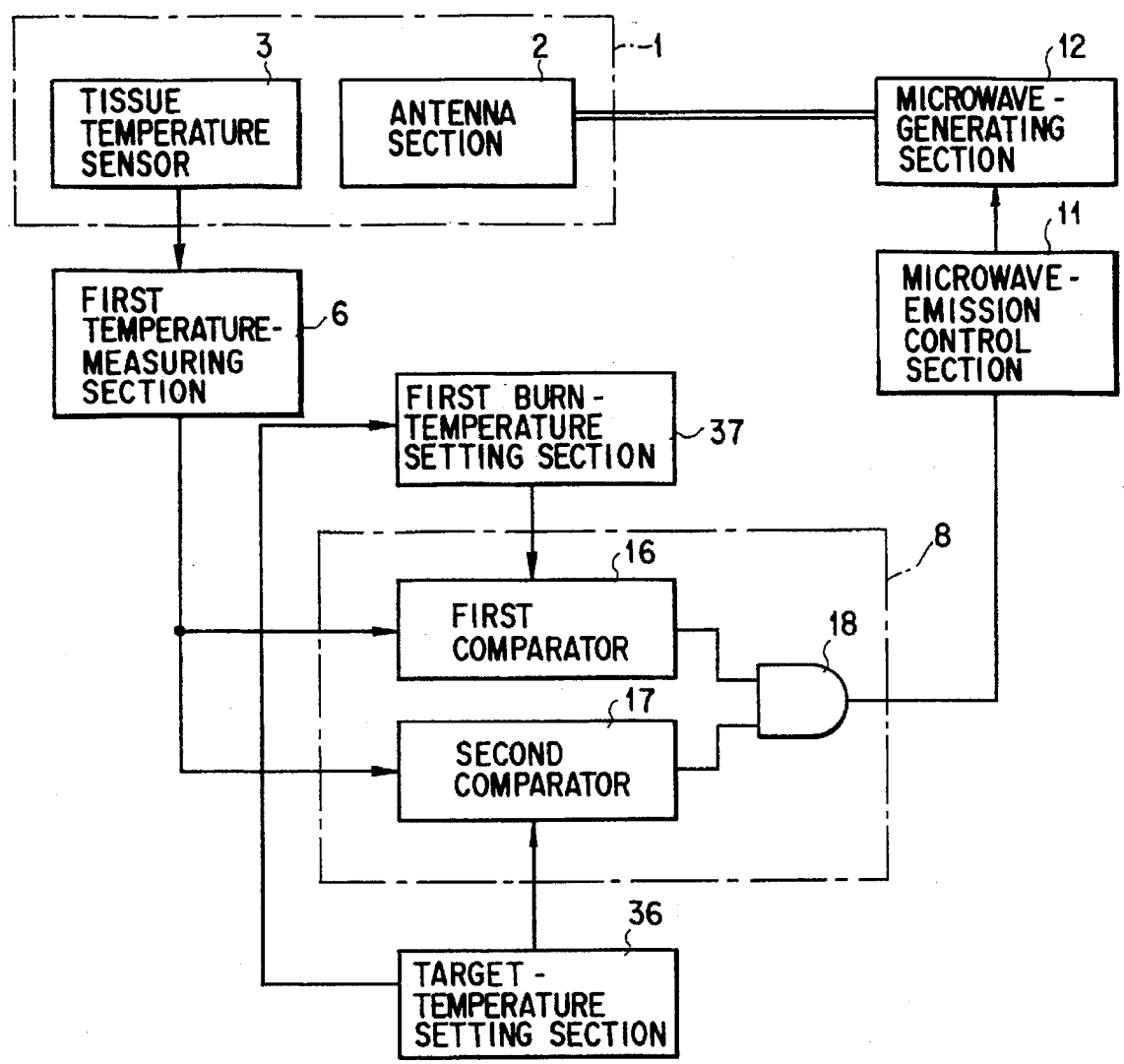
F I G. 10

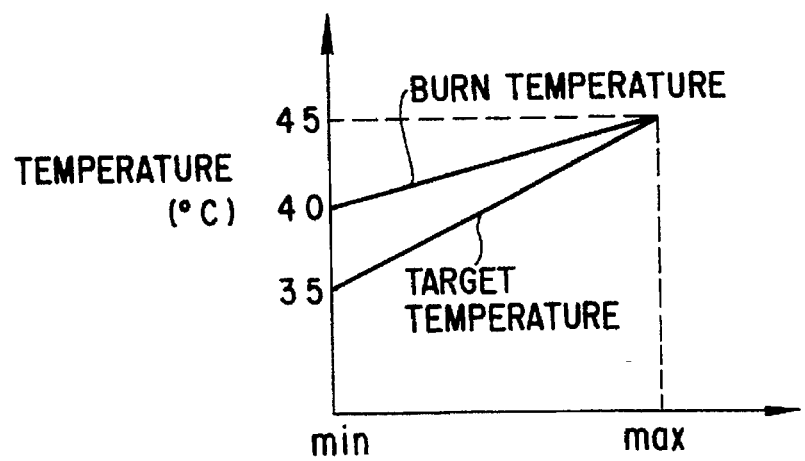
F I G. 11
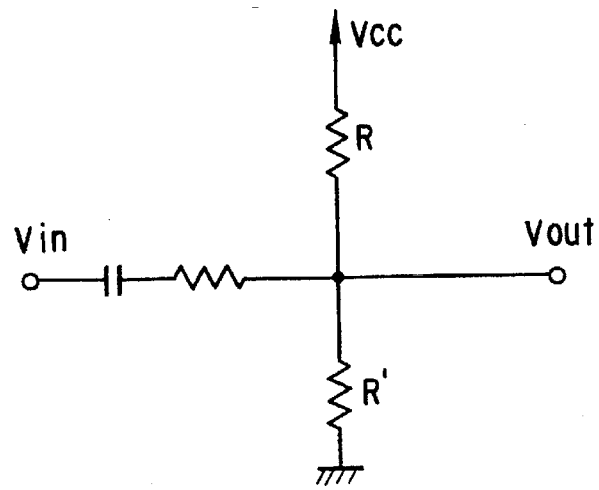
F I G. 12
| Vin | Vout |
|---|---|
| 35 °C | 40 °C |
| 37 | 41 |
| 39 | 42 |
| 41 | 43 |
| 43 | 44 |
| 45 | 45 |
F I G. 13

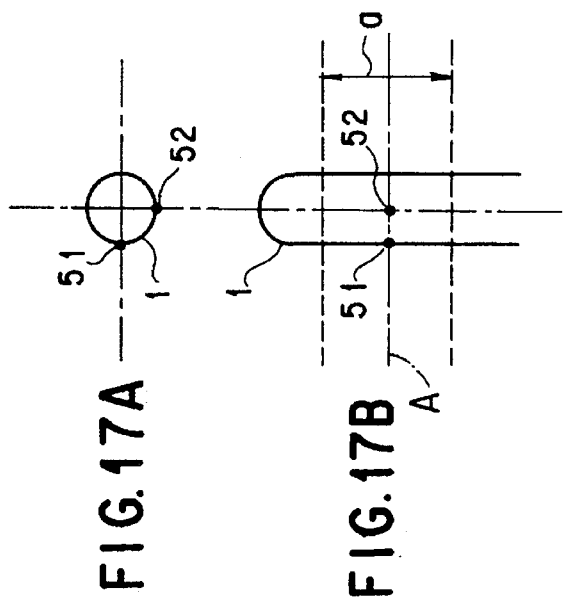
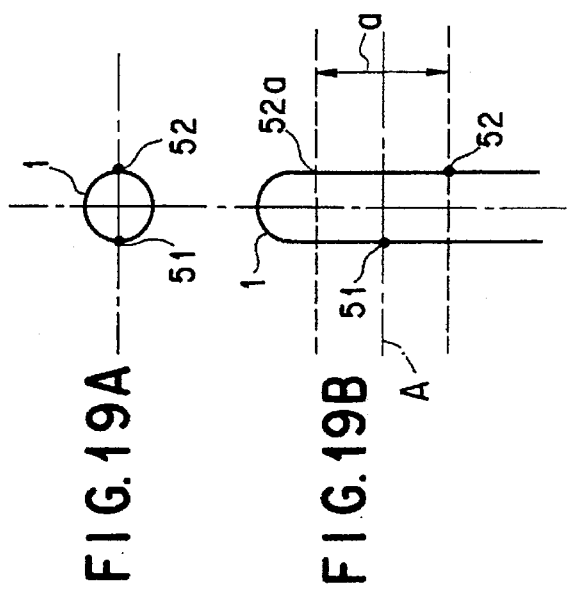
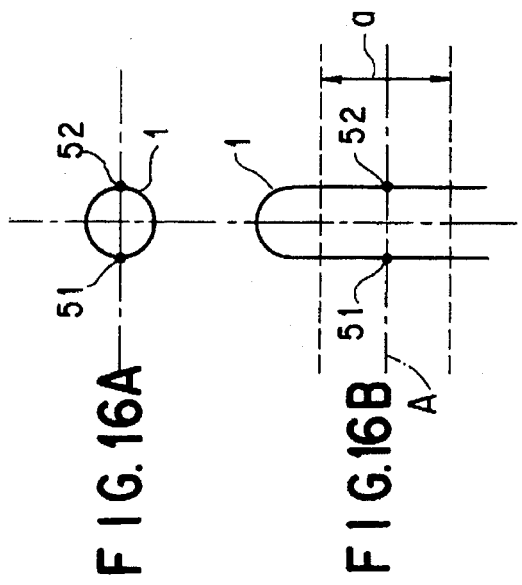
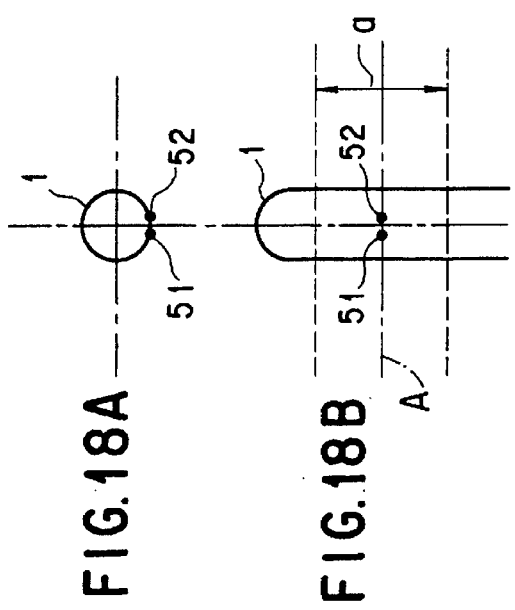

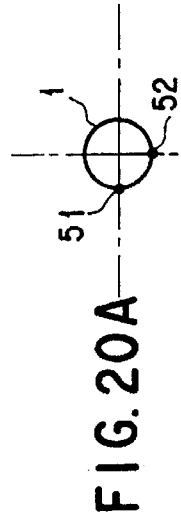
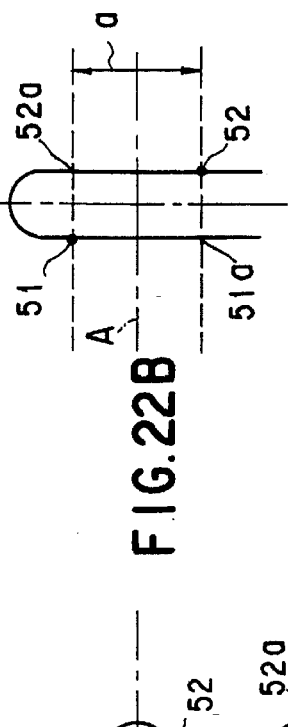
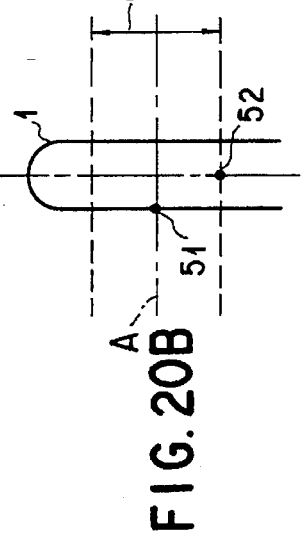
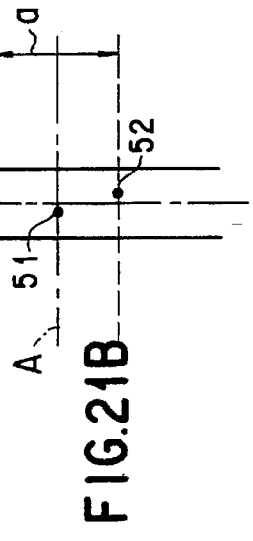
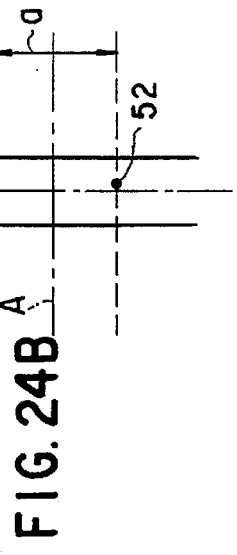
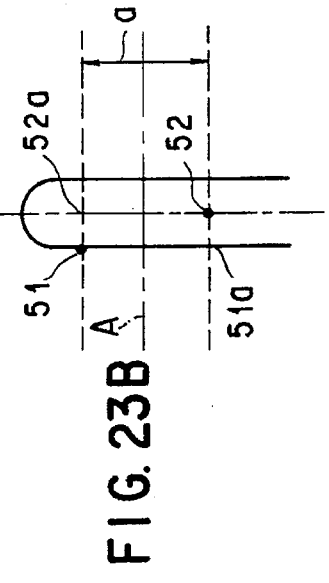

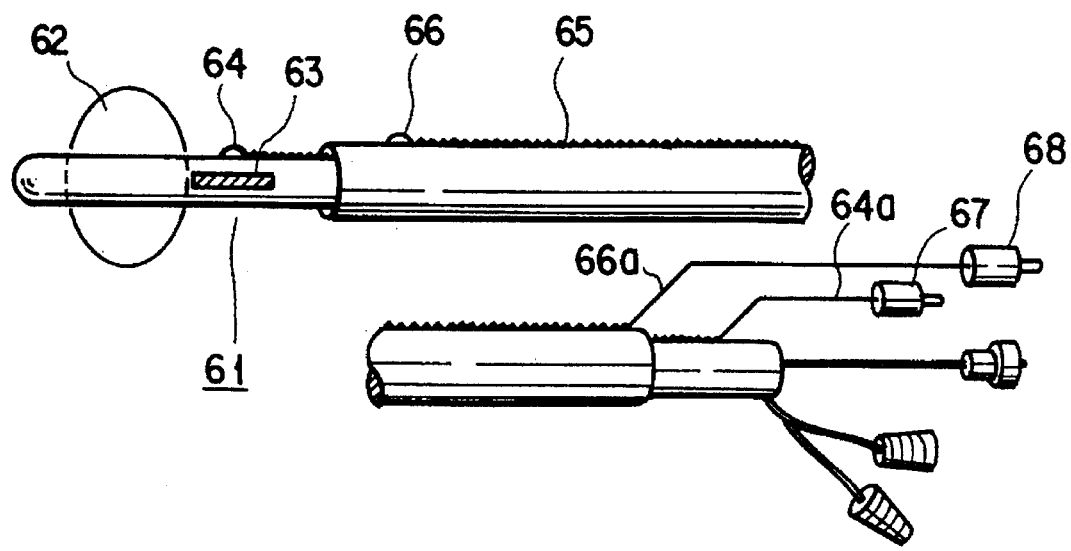
F I G. 25
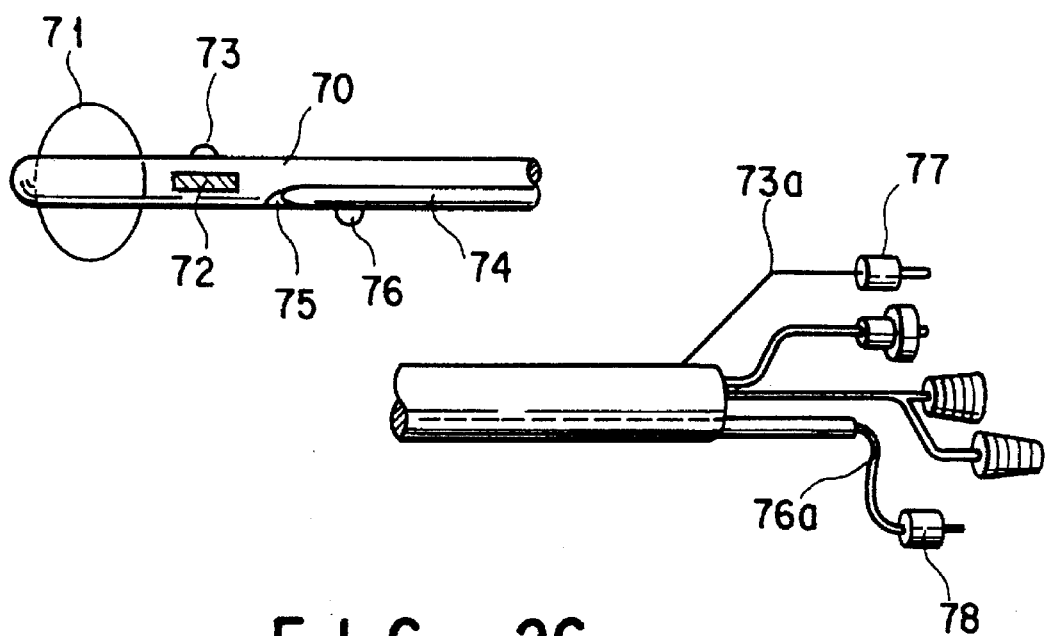
F I G. 26

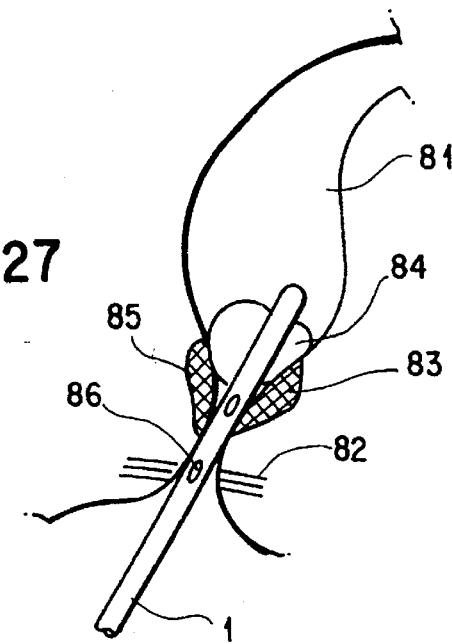
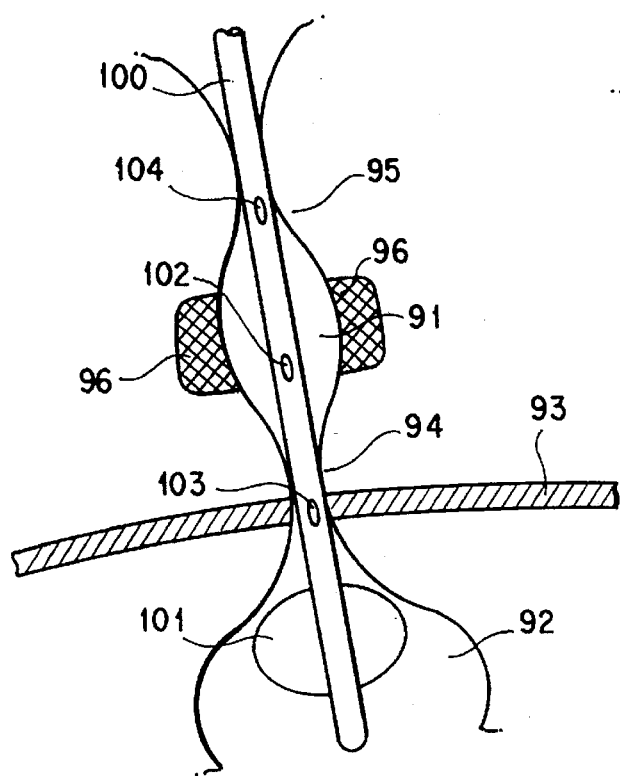
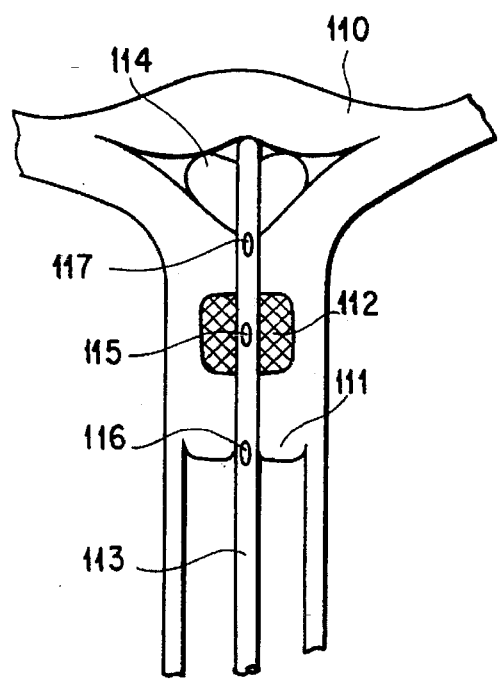

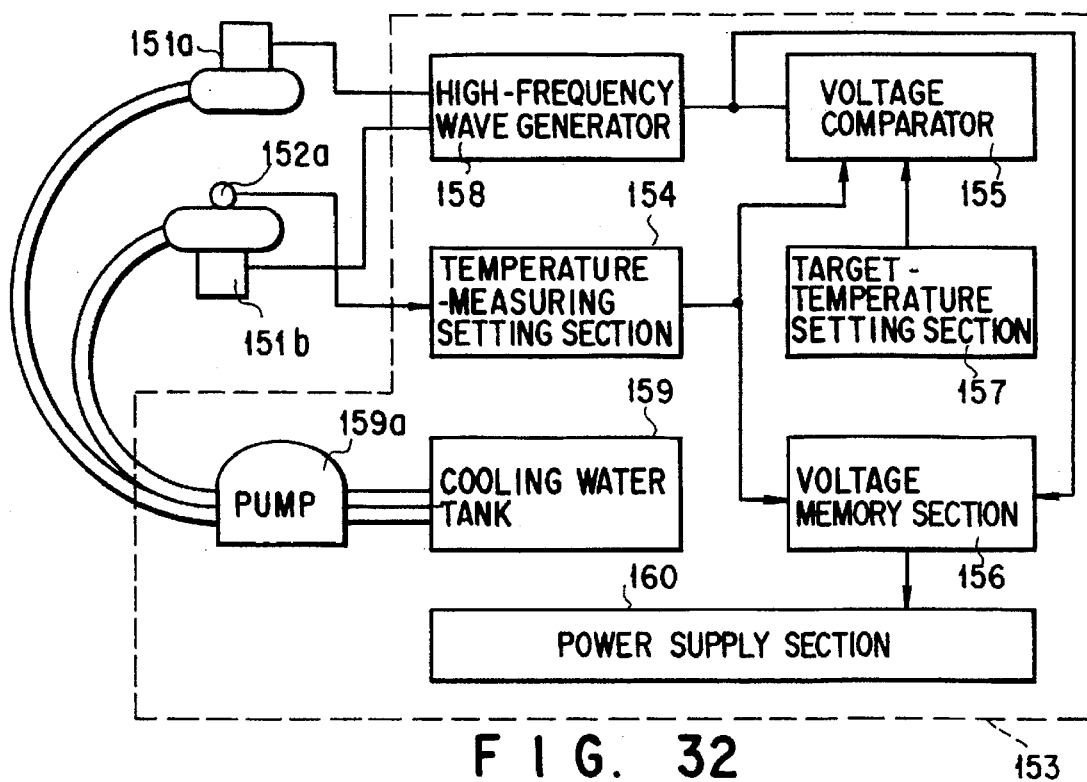
F I G. 32
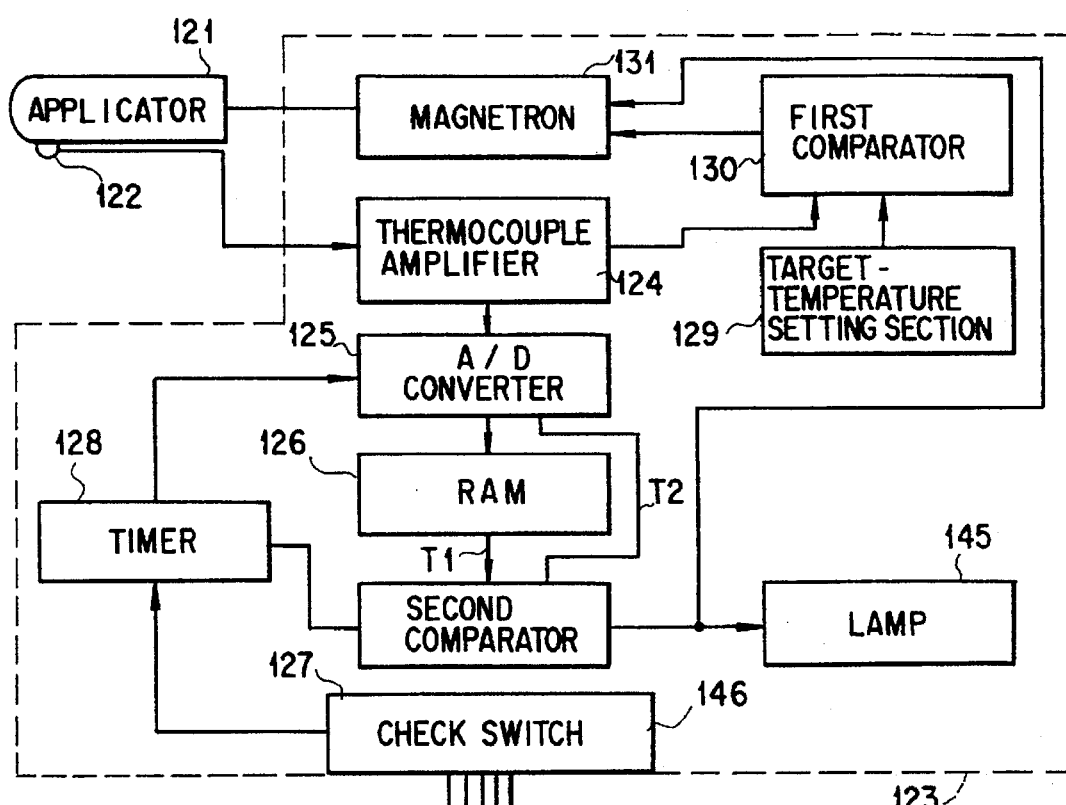
F I G. 33

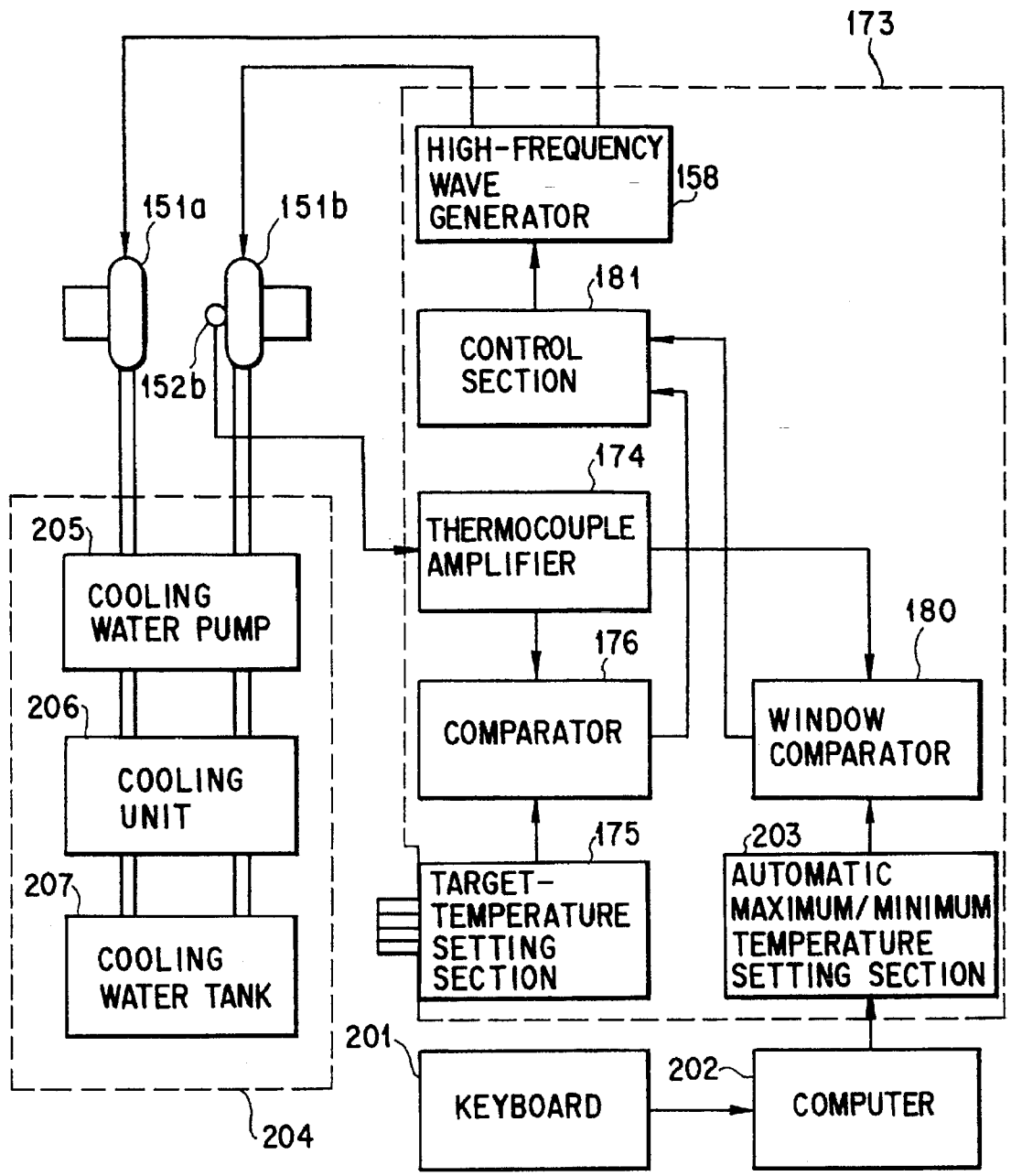
F I G. 38

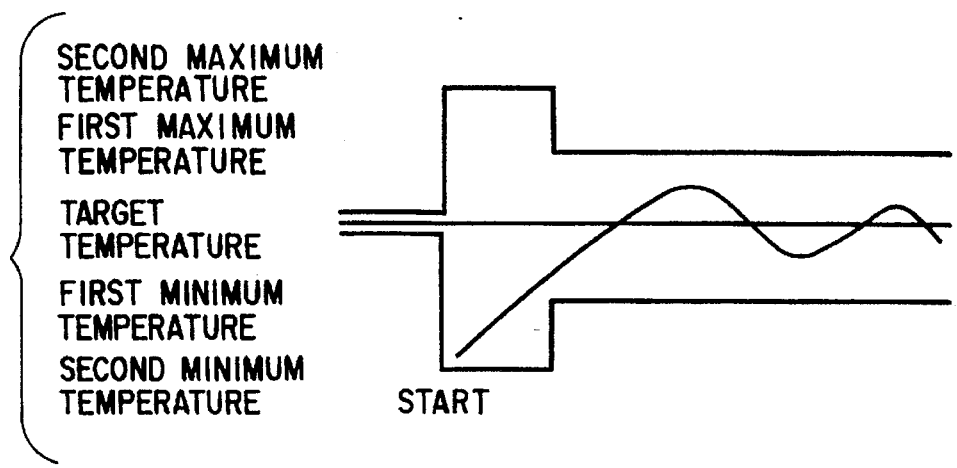
F I G. 39
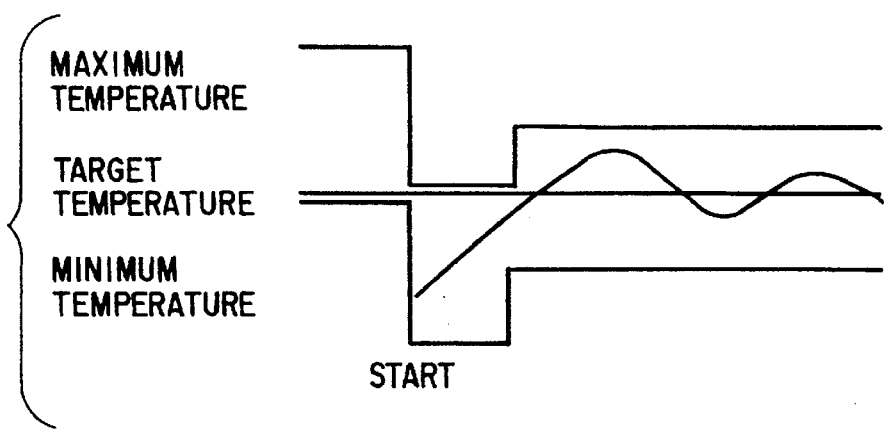
F I G. 40
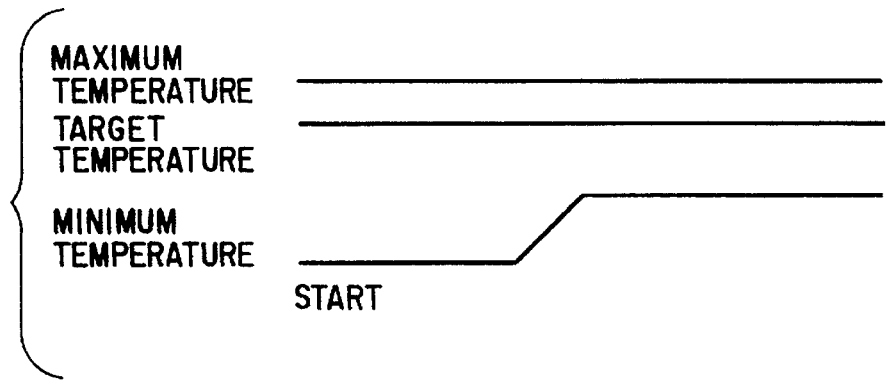
F I G. 41

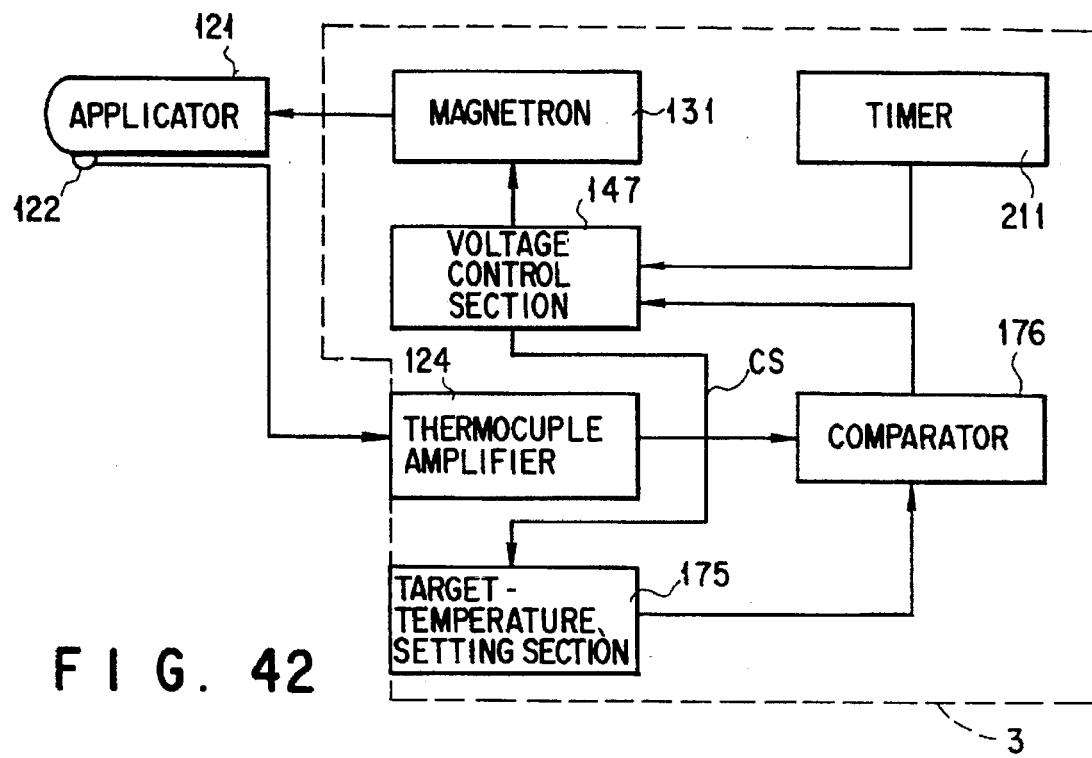
F I G. 42
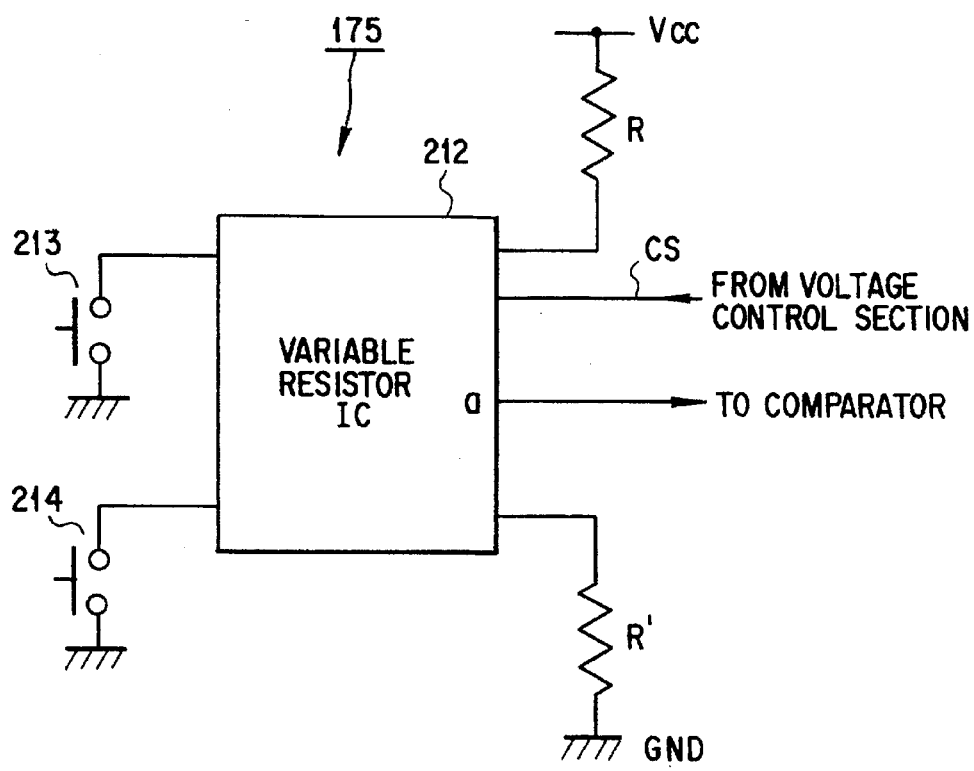
F I G. 43

ELECTROMAGNETIC-WAVE THERMATOLOGICAL DEVICE

This application is a continuation of application Ser. No. 08/241,298, filed May 11, 1994, (now abandoned).

BACKGROUND OF THE INVENTION

1. Field of the Invention

The present invention relates to a thermatological device for applying electromagnetic waves to an affected part to heat the part to a target temperature, thereby to thermatologically treat the affected part.

2. Description of the Related Art

Thermatological devices which apply microwaves to an affected part in a body cavity to heat the part, thereby to thermatologically treat the affected part, are well known. Devices of this type are disclosed in, for example, Jpn. UM Appln. KOKAI Publication No. 63-182759 and Jpn. Pat. Appln. KOKAI Publication No. 2-41976.

A thermatological device of this type comprises an applicator which contains an antenna section and a temperature sensor. The applicator is inserted into a body cavity in which an affected part is present, and microwaves are emitted from the antenna section to the affected part. Irradiated with the microwaves, the affected part is heated and, thus, thermatologically treated. The temperature sensor detects the surface temperature of the parts which the applicator contacts in the body cavity. In accordance with the temperature detected, the emission of microwaves is controlled, heating the affected part to a target temperature.

When the applicator is inserted into, for example, the urethra in order to cure prostatomegaly, it contacts the urethral muscosal membrane. To prevent burn of the urethral muscosal membrane while heating the interior of the prostate to a higher temperature than the muscosal membrane, cooling water is circulated in the applicator. The cooling water can be circulated at an increased rate, to thereby heat the interior of the prostate to a high temperature, without burning the urethral muscosal membrane. This method of circulating the cooling water helps to enhance the effect of thermatological treatment.

Some of the parts located around the prostate must be protected from burn at all cost. Hence, when the temperature ambient to the prostate rises too much, the microwave emission is stopped, thereby interrupting the thermatological treatment on the prostate.

During the thermatological treatment of an affected part, the temperature sensor must be held in contact with the part. However, the sensor may be displaced from the part by some cause. If the treatment is continued, with the sensor displaced from the affected portion, the temperature of the affected portion will differ from a target value, and the thermatological treatment will not be successfully accomplished.

SUMMARY OF THE INVENTION

An object of the present invention is to provide a magnetic-wave thermatological device for applying electromagnetic waves to an affected part, which stops applying the electromagnetic waves when the temperature of any other part adjacent to the affected part rises above a predetermined value and which is therefore highly safe.

Another object of the invention is to provide a magnetic-wave thermatological device for applying electromagnetic waves to an affected part, which stops emitting electromagnetic waves if the part fails to reach a target temperature within a predetermined time from the start of application of the electromagnetic waves.

To achieve these objects, according to the present invention there is provided a magnetic-wave thermatological device which comprises: an applicator capable of being inserted into a body cavity and having a temperature sensor and a wave-applying section for applying electromagnetic waves to an affected part; a wave-generating section for generating and supplying electromagnetic waves to the wave-applying section; and a temperature control section for controlling the wave-generating section in accordance with the temperature detected by the temperature sensor.

The electromagnetic-wave thermatological device according to the present invention can stop applying electromagnetic waves when the temperature of any other part adjacent to the affected part rises above a predetermined value and which is therefore highly safe.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 10 is a block diagram showing a microwave thermatological device according to a fourth embodiment of this invention;

FIG. 11 is a graph representing the relationship between the target temperature and the first burn temperature which are set in the thermatological device shown in FIG. 10;

FIG. 12 is a diagram showing a circuit for setting the gradient of the first burn temperature and that of the target temperature in the device illustrated in FIG. 10;

FIG. 13 is a table indicating the relationship between the input voltage Vin and output voltage Vout of the circuit shown in FIG. 12;

FIG. 16A and 16B are a plan view and a side view of an applicator, illustrating a positional relationship two temperature sensors may assume on the applicator;

FIGS. 17A and 17B are a plan view and a side view of the applicator, showing another positional relationship the temperature sensors may have on the applicator;

FIGS. 18A and 18B are a plan view and a side view of the applicator, representing still another positional relationship the temperature sensors may assume on the applicator;

FIGS. 19A and 19B are a plan view and a side view of the applicator, showing another positional relationship the temperature sensors may take on the applicator;

FIGS. 20A and 20B are a plan view and a side view of the applicator, illustrating a specific positional relationship of the temperature sensor mounted on the applicator;

FIGS. 21A and 21B are a plan view and a side view of the applicator, representing a particular positional relationship of the temperature sensor mounted on the applicator;

FIGS. 22A and 22B are a plan view and a side view of the applicator, illustrating another positional relationship of the temperature sensor mounted on the applicator;

FIGS. 23A and 23B are a plan view and a side view of the applicator, illustrating still another positional relationship of the temperature sensor mounted on the applicator;

FIGS. 24A and 24B are a plan view and a side view of the applicator, illustrating a particular positional relationship of the temperature sensor mounted on the applicator;

FIG. 25 is an exploded perspective view of the applicator;

FIG. 26 is an exploded perspective view of an applicator of another type;

FIG. 27 is a sectional view of the rectum, for explaining how the device of this invention is used to perform thermatological treatment on the rectum;

FIG. 28 is a sectional view showing the esophagus, the stomach and the diaphragm, and explaining how a device of the present invention is used to perform thermatological treatment in the esophagus;

FIG. 29 is a sectional view of the uterus, for explaining how the device of this invention is used to perform thermatological treatment in the uterus;

FIG. 32 is a block diagram showing a hyperthermia device which is a ninth embodiment of the present invention;

FIG. 33 is a block diagram illustrating another hyperthermia device which is a tenth embodiment of this invention;

FIG. 38 is a block diagram showing a hyperthermia device which is a thirteenth embodiment of the present invention;

FIG. 39 is a timing chart showing how a maximum temperature and a minimum temperature change in a specific fashion with respect to a target temperature in the thirteenth embodiment of the invention;

FIG. 40 is a timing chart illustrating how a maximum temperature and a minimum temperature change in another fashion with respect to a target temperature in the device of FIG. 39;

FIG. 41 is a timing chart showing how a maximum temperature and a minimum temperature change in a still another fashion with respect to a target temperature in the device of FIG. 39;

FIG. 42 is a block diagram showing a hyperthermia device which is a fourteenth embodiment of the present invention; and FIG. 43 is a circuit diagram showing the target-temperature setting section incorporated in the device illustrated in FIG. 42.

DETAILED DESCRIPTION OF THE PREFERRED EMBODIMENTS

An embodiment of the present invention, which is a microwave thermatological device, will now be described with reference to FIGS. 1 to 6.

Figure 1:
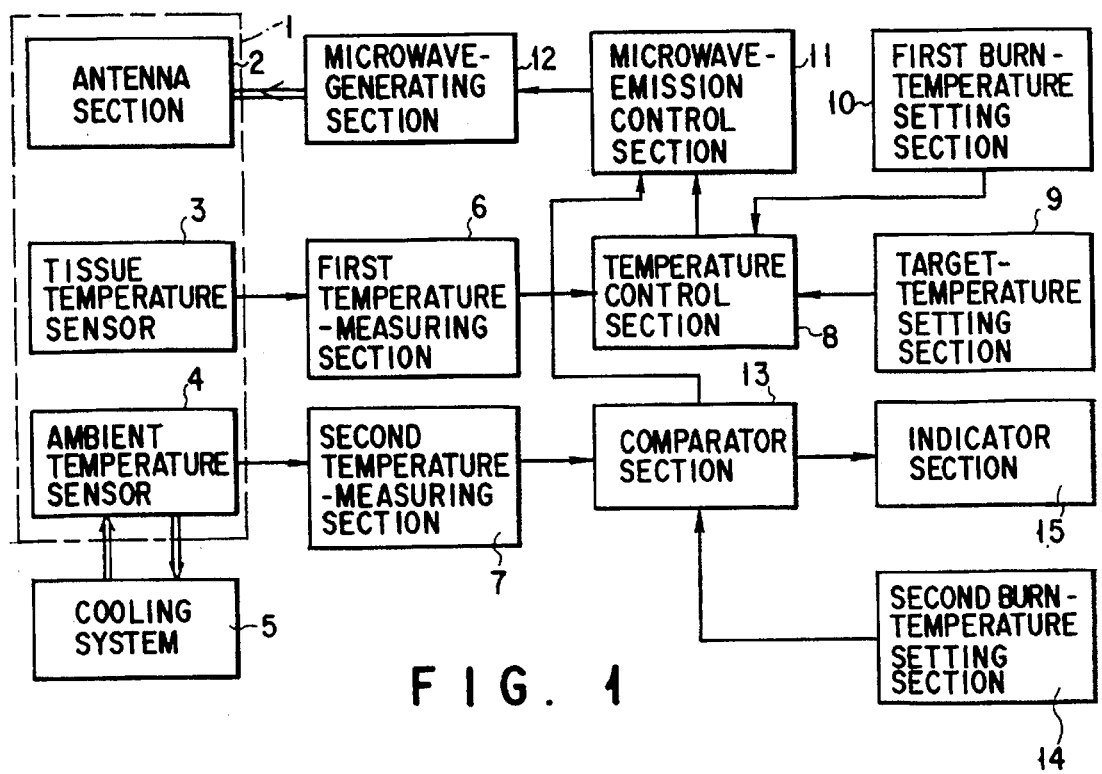
FIG. 1 is a block diagram showing a microwave thermatological device according to a first embodiment of the present invention.

As shown in FIG. 1, the thermatological device comprises an applicator 1 which includes an antenna section 2, a temperature sensor 3 and an ambient temperature sensor 4. The antenna section 2 is designed to emit microwaves. The temperature sensors 3 and 4 are spaced apart from each other in the axial direction of the applicator 1. Each temperature sensor comprises a thermocouple, thermistor, an optical-fiber thermometer, or the like.

A cooling system 5 is coupled to the applicator 1 to circulate cooling water in the applicator 1.

The thermatological device further comprises a first temperature-measuring section 6, a second temperature-measuring section 7, a temperature control section 8, a target-temperature setting section 9, a first burn-temperature setting section 10, a microwave-emission control section 11, a microwave-generating section 12, a comparator section 13, a second burn-temperature setting section 14, and an alarm-generating section 15.

The first temperature-measuring section 6 is connected to the temperature sensor 3, and the second temperature-measuring section 7 to the ambient temperature sensor 4. The first temperature-measuring section 6 amplifies a signal output from the temperature sensor 3 and representing the temperature the sensor 3 has detected. The signal amplified by the section 6 is supplied to the temperature control section 8.

Input to the temperature control section 8 are three signals. The first signal has been supplied from the target-temperature setting section 9 and represents the target temperature (e.g., 39° C.) set by operating the section 9. The second signal has been supplied from the first burn-temperature setting section 10 and represents the first burn temperature (e.g., 45° C.) set by operating the section 10. The third signal has been generated by the first temperature-measuring section 6 and represents the temperature which the temperature sensor 3 has detected of the parts being heated. The temperature control section 8 finds the difference between the temperature of the affected part and the target temperature and also the difference between the temperature of the affected part and the first burn temperature, and generates two signals representing these temperature differences. The signals are supplied from the section 8 to the microwave-emission control section 11. The section 11 produces a control signal from the two input signals. The control signal is input to the microwave-generating section 12, thereby controlling the section 12. More specifically, the microwave-generating section 12 starts generating microwaves when the control signal rises to a high level and stops generating the waves when the control signal falls to a low level. The microwaves generated by the section 12 is supplied to the antenna section 2 of the applicator 1. The antenna section 2 emits the microwaves to an affected part.

The ambient temperature sensor 4 detects the temperature of a part adjacent to the affected part being irradiated with the microwaves and being thus heated. The second temperature-measuring section 7 generates a signal which represents the temperature of the adjacent part. This signal is input to the comparator section 13. Also input to the comparator section 13 is a signal representing the second burn temperature (e.g., 42° C.) set by operating the second burn-temperature setting section 14. The comparator section 13 compares these input signals and produces a signal which is at a level determined by the relationship between the temperature of the adjacent part and the second burn temperature. The signal is supplied to the microwave-emission control section 11.

The comparator section 13 is connected to the alarm-generating section 15. The section 15 generates a visual or audio alarm when the temperature detected by the ambient temperature sensor 4 reaches the second burn temperature.

Figure 2:
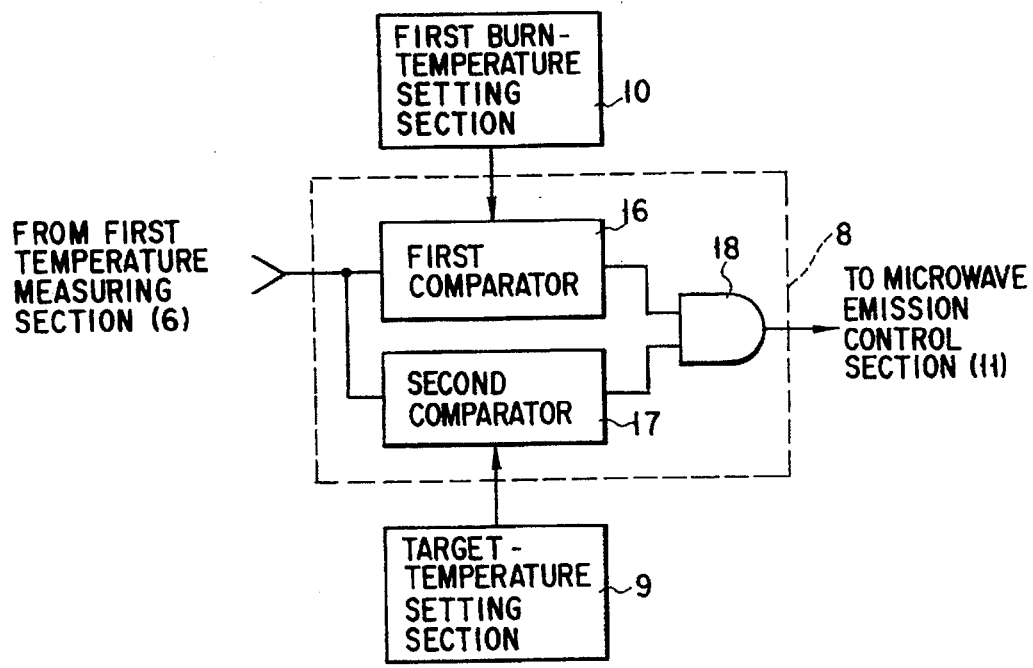
FIG. 2 is a block diagram showing the target-temperature setting section incorporated in the device illustrated in FIG. 1.

The temperature control section 8 will be described in detail, with reference to FIG. 2. As shown in FIG. 2, the section 8 comprises a first comparator 16, a second comparator 17 and an AND circuit 18.

The first comparator 16 receives the signal output from the first temperature-measuring section 6 and representing the temperature of the affected part, and also the signal output from the first burn-temperature setting section 10 and representing the first burn temperature. The first comparator 16 compares these input signals and generates a high-level signal if the temperature of the affected part is lower than the first burn temperature.

Meanwhile, the second comparator 17 receives the signal output from the first temperature-measuring section 6 and representing the temperature of the affected part, and also the signal output from the signal output from the target-temperature setting section 9 and representing the target temperature. The second comparator 17 compares the input signals and generates a high-level signal if the temperature of the affected part is lower than the target temperature.

The AND circuit 18 receives the signals generated by the comparators 16 and 17 and generates a signal representing the logic product of the two input signals. The signal generated by the AND circuit 18 is supplied to the microwave-emission control section 11.

The operation of the first embodiment of this invention will now be explained, with reference to FIGS. 3 to 6.

Figure 3:
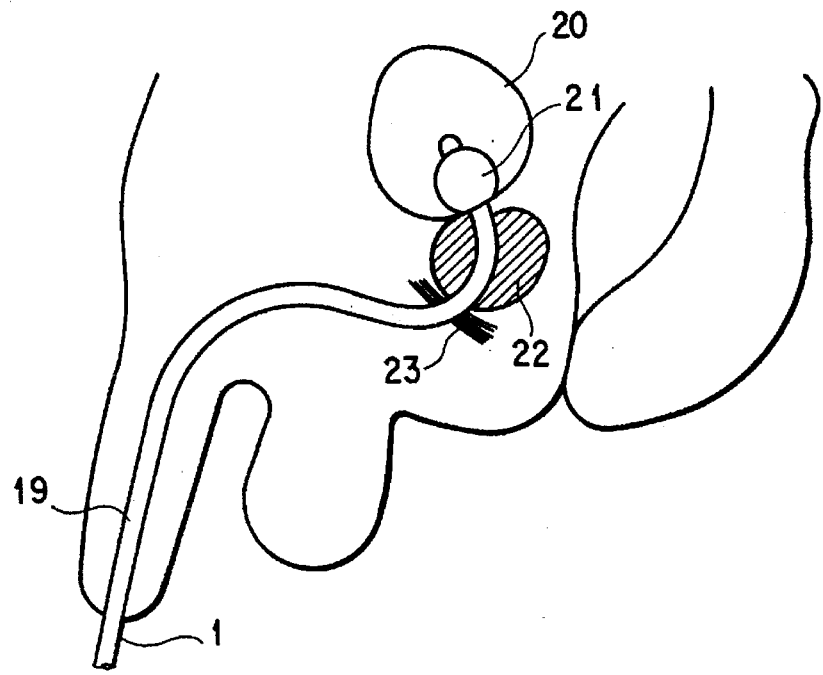
FIG. 3 is a sectional view of some organe of a patient, representing the position in one of these organs, where the applicator of the device is located during the use of the device.
Figure 4:
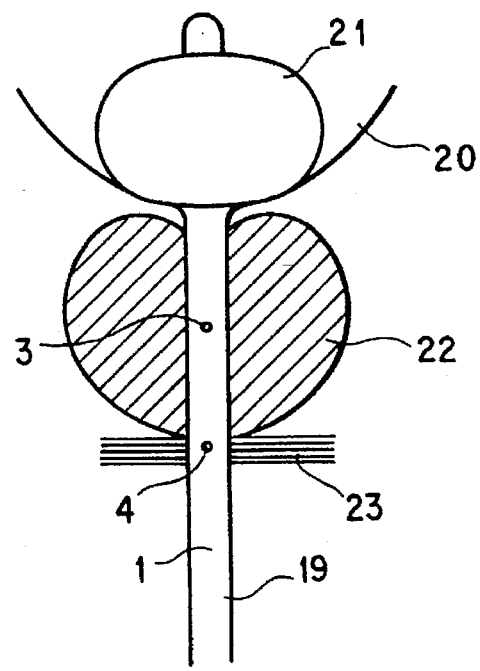
FIG. 4 is a sectional view of the organs, showing the position in one of these organs, which the temperature sensor of the device is located during the use of the device.

First, as shown in FIG. 3, the applicator 1 is inserted into the urethra 19 until its distal end reaches the bladder 20. The position of the applicator 1 is adjusted, thus locating the temperature sensor 3 at the prostate 22 which must be treated, and the ambient temperature sensor 4 near the sphincter muscle 23 which must be protected from burn, as is illustrated in FIG. 4. Then, the balloon 21 mounted on the distal end portion of the applicator 1 is inflated, whereby the applicator 1 is held in the urethra 19, with the temperature sensors 3 and 4 positioned at the prostate 22 and near the sphincter muscle 23, respectively.

Thereafter, the microwave-emission control section 11 is operated, thereby generating and supplying a control signal to the microwave-generating section 12. While the control signal is at the high level, the section 12 generates microwaves, which is emitted from the antenna section 2. When the control signal falls to the low level, the section 12 stops generating microwaves. The antenna section 2 applies the microwaves onto the prostate 22. When the control signal falls to the low level, the section 12 stops generating microwaves.

Figure 5:
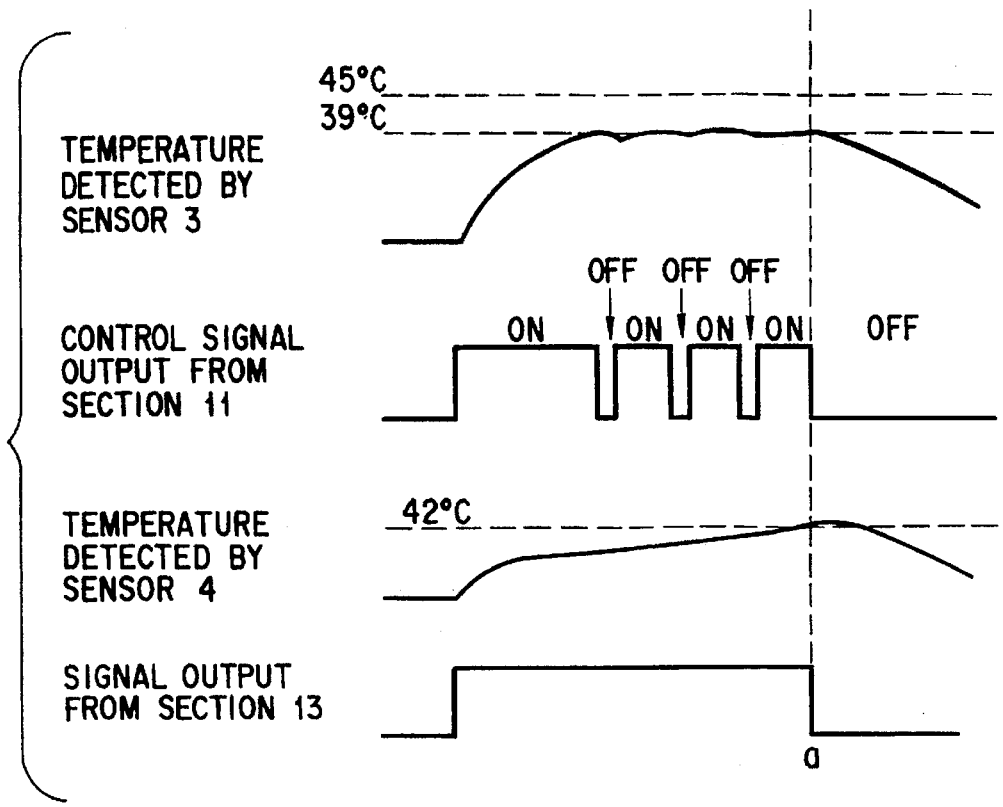
FIG. 5 is a timing chart explaining the operation of the thermatological device shown in FIG. 1.
Figure 6:
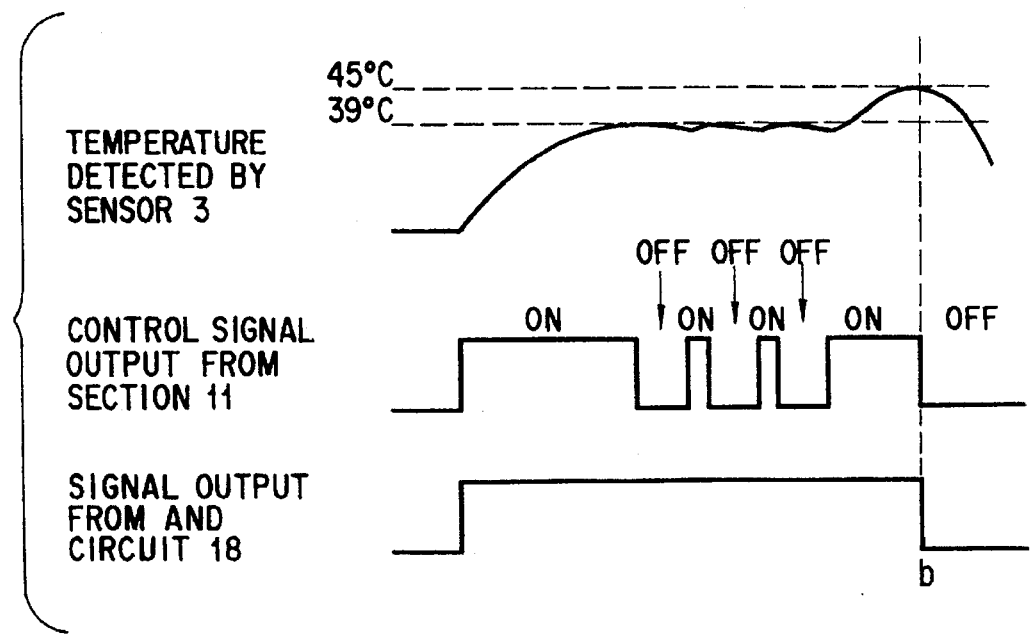
FIG. 6 is another timing chart explaining the operation of the thermatological device.

As microwaves are applied from the antenna section 1 onto the prostate 22, the prostate 22 is heated, and the temperatures detected by the temperature sensors 3 and 4 gradually rise as illustrated in FIGS. 5. When the temperature of the prostate 22, which is detected by the temperature sensor 3, reaches the target value (39° C.), the output signal of the second comparator 17 (FIG. 2) falls to the low level. Therefore, the output signal of the temperature control section 8 falls to the low level, and so does the output signal of the microwave-emission control section 11. As a result, the microwave-generating section 12 stops generating microwaves, and the temperature of the prostate 22 gradually decreases.

When the temperature detected by the temperature sensor 3 falls below the target value (39° C.), the output signal of the second comparator 17 rises to the high level. Hence, the output signal of the temperature control section 8 rises to the high level, and so does the output signal of the microwave-emission control section 11. The microwave-generating section 12 starts generating microwaves, which are applied from the antenna section 2 onto the prostate 22. The prostate 22 is heated.

Thereafter, the temperature control section 8 controls the microwave-emission control section 11 as shown in FIG. 5—in accordance with the relationship which the output signal of the first temperature-measuring section 6 has with the output signal of the target-temperature setting section 9.

While the temperature of the prostate 22 is being controlled as described above, the comparator section 13 keeps comparing the temperature detected by the ambient temperature sensor 4 with the second burn temperature (42° C.) set by operating the second burn-temperature setting section 14. The comparator section 13 generates a signal which is at a level which depends on, as described above, the relationship between the temperature of the adjacent part and the second burn temperature. More precisely, the output signal of the section 13 is at a high level when the temperature detected by the sensor 4 is lower than the second burn temperature, and is at a low level when that temperature is equal to or higher than the second burn temperature. Hence, the output signal of the control section 11 falls to the low level at time a after the start of the heating, when the temperature detected by the temperature detected by the sensor 4 rises to or above the second burn temperature. As a result, the microwave-generating section 12 stops generating microwaves. No microwaves are now applied from the antenna section 2 onto the prostate 22. Meanwhile, the output signal of the comparator section 13, which is at the low level, is supplied to the alarm-generating section 15. Therefore, the section 15 generates a visual or audio alarm when the temperature detected by the ambient temperature sensor 4 reaches the second burn temperature.

As described above, the microwave-generating section 12 is controlled in accordance with the temperature of the affected part, detected by the temperature sensor 3, thereby heating the affected part to the preset target temperature, and the section 12 stops generating microwaves when the temperature of the part adjacent to the affected part, detected by the ambient temperature sensor 4, reaches the second burn temperature. Therefore, the affected part can be effectively treated thermatologically, and the adjacent parts is protected from burn.

The operation of the microwave thermatological device has been explained on the assumption that the output signal of the first comparator 16 is always at the high level—that is, the temperature detected by the temperature sensor 3 is always below the first burn temperature (e.g., 45° C.). Nonetheless, even if temperature detected by the sensor 3 reaches the first burn temperature at time b after the start of the heating, the output signal of the first comparator 16 falls to the low level. As a result, the control signal output from the control section 11 falls to the low level, whereby the microwave-generating section 12 stops generating microwaves.

Thus should the output signal of the second comparator 17 remains at the low level for some reason, the output signal of the first comparator 16 falls to the low level when the temperature detected by the temperature sensor 3 (i.e., the temperature of the affected part) reaches the first burn temperature set by operating the first burn-temperature setting section 10. This prevents excessive heating of the affected part which may occur when the second comparator 17 fails to perform its function.

As described above, the microwave-generating section 12 stops generating microwaves the moment the temperature detected by the ambient temperature sensor 4 rises to or above the second burn temperature, thereby interrupting the heating of the affected part and the adjacent part. Instead, the section 12 may be so controlled as to reduce the microwave emission when the temperature detected by the sensor 4 rises to or above the second burn temperature.

A microwave thermatological device, which is the second embodiment of the invention, will be described below, with reference to FIGS. 7 and 8.

This thermatological device has two ambient temperature sensors 24 and 25, whereas the device according to the first embodiment has one ambient temperature sensor. The first ambient temperature sensor 24 is located on the applicator 1, while the second ambient temperature sensor 25 away from the applicator 1. As in the first embodiment, a temperature sensor 3 is provided on the applicator 1. The temperature sensor 3 and the first ambient temperature sensor 24 are spaced apart from each other in the axial direction of the applicator 1.

The first ambient temperature sensor 24 performs the same function as the ambient temperature sensor 4 of the first embodiment. When the temperature the sensor 24 detects rises to or above the second burn temperature, emission of microwaves is automatically interrupted. Also, when the temperature the second ambient temperature sensor 25 detects rises to a third burn temperature, emission of microwaves is automatically interrupted.

Of the components of the second embodiment, those which are identical or similar to those of the first embodiment are designated at the same reference numerals in FIG. 7 and will not be explained in detail in the following description.

Figure 7:
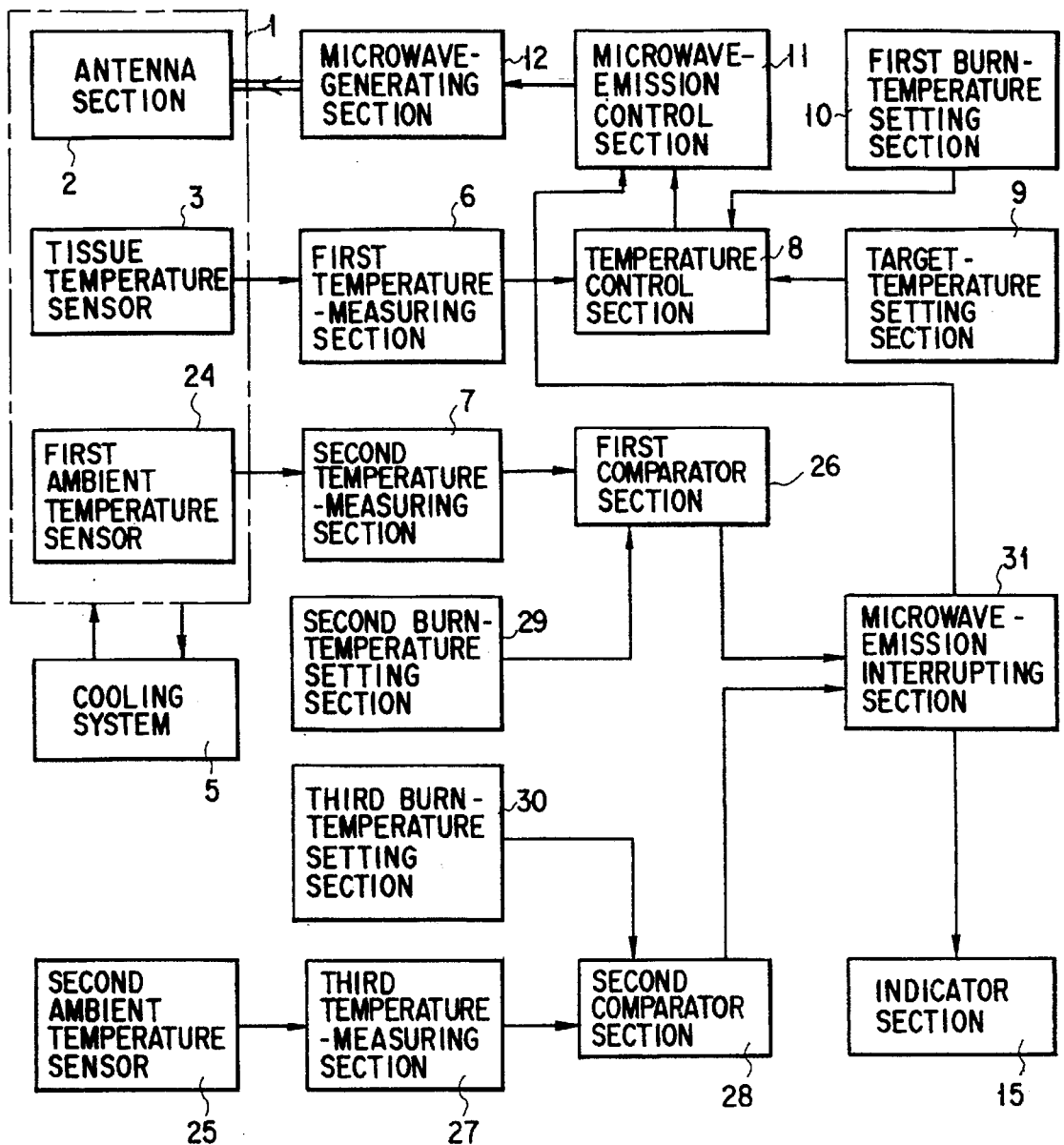
FIG. 7 is a block diagram illustrating a microwave thermatological device according to a second embodiment of the present invention.

As shown in FIG. 7, a second temperature-measuring section 7 is connected to the first ambient temperature sensor 24. The first ambient temperature sensor 24 detects the temperature of a part adjacent to an affected part. The second temperature-measuring section 7 generates a signal which represents the temperature of the adjacent part. The signal is supplied to a first comparator section 26. The section 26 compares the temperature of the adjacent part with the second burn temperature (e.g., 42° C.) set by operating a second burn-temperature setting section 29. It produces a signal which is at a high level while the temperature detected by the first ambient temperature sensor 24 remains lower than the second burn temperature (42° C.). The signal is supplied to a microwave-emission interrupting section 31.

Located away from the applicator 1, the second ambient temperature sensor 25 detects the temperature of a part of an organ present outside the applicator 1. The sensor 25 is connected to a third temperature-measuring section 27. The section 27 generates a signal representing the temperature detected by the sensor 25. The signal is input to a second comparator section 28. The second comparator section 28 compares the temperature of the adjacent part with the third burn temperature (e.g., 43° C.) set by operating a third burn-temperature setting section 30. It produces a signal which is at a high level while the temperature detected by the second ambient temperature sensor 25 remains lower than the third burn temperature (43° C.). This signal is supplied to a microwave-emission interrupting section 31.

The microwave-emission interrupting section 31 produces a logic product of the output signals of the comparator sections 26 and 28. The output signal of the section 31 is supplied to a microwave-emission control section 11 and also to a alarm-generating section 15. The section 15 generates a visual or audio alarm when the output signal of the microwave-emission interrupting section 31 falls to a low level.

The first ambient temperature sensor 24 and the second ambient temperature sensor 25 are each a thermocouple, thermistor, an optical-fiber thermometer, or the like.

The operation of the second embodiment of the invention will now be explained, with reference to FIG. 8.

Figure 8:
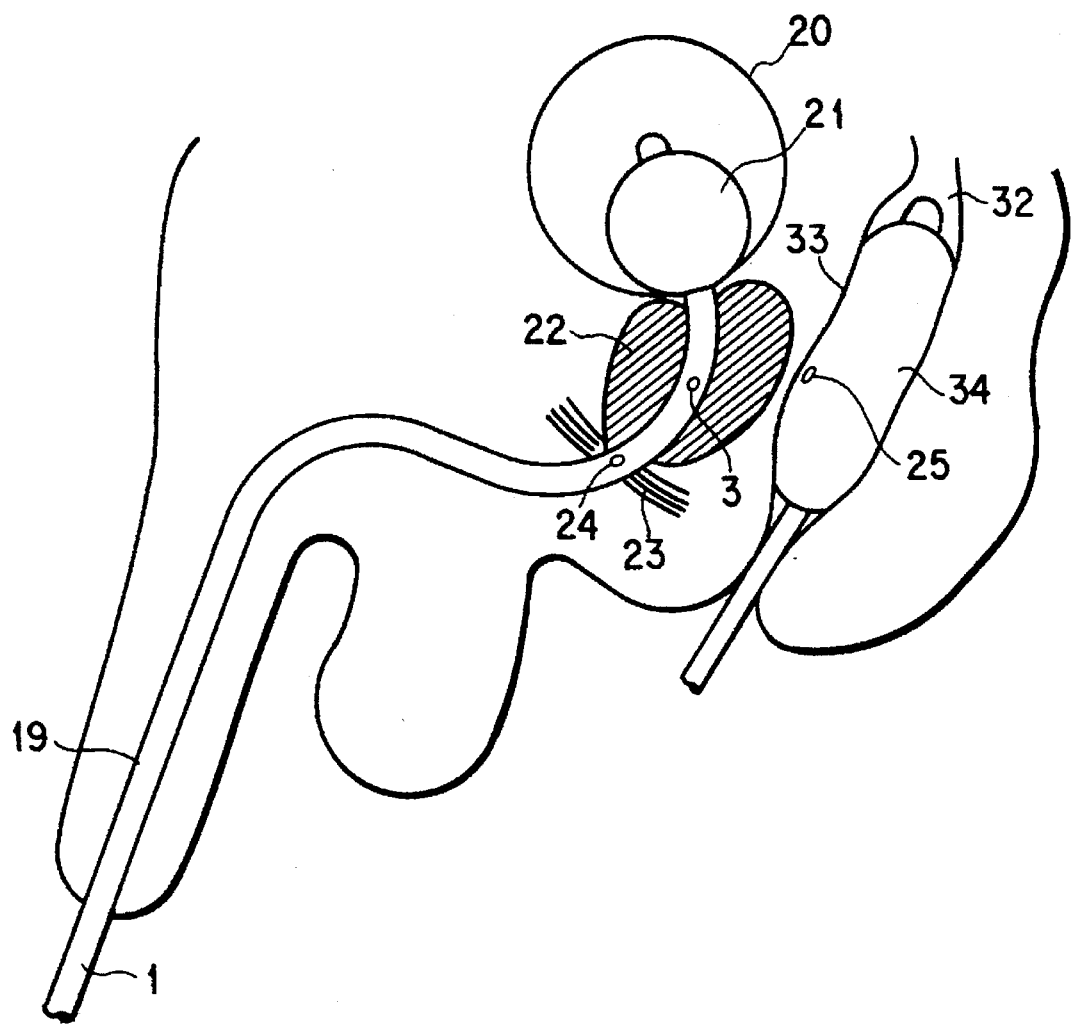
FIG. 8 is a sectional view of some organs of a patient, for representing the positions in these organs, where the applicator, temperature sensor, first burn temperature sensor and second burn temperature sensor of the device shown in FIG. 7 are located during the use of the device.

First, as shown in FIG. 8, the applicator 1 is inserted into the urethra 19 until its distal end reaches the bladder 20. The position of the applicator 1 is adjusted, thus locating the temperature sensor 3 at the prostate 22 which must be treated, and the first ambient temperature sensor 24 near the sphincter muscle 23 which must be protected from burn, as is illustrated in FIG. 8. Then, the balloon 21 mounted on the distal end portion of the applicator 1 is inflated, whereby the applicator 1 is held in the urethra 19, with the temperature sensors 3 and 24 positioned at the prostate 22 and the sphincter muscle 23, respectively.

The second ambient-temperature sensor 25, with a balloon 34 mounted on its circumferential surface, is inserted into the rectum 32. The balloon 34 is inflated, and the sensor 25 is thereby held in the rectum 32.

Thereafter, the microwave-emission control section 11 is operated, generating and supplying a control signal to the microwave-generating section 12. While the control signal is at the high level, the section 12 generates microwaves, which is emitted from the antenna section 2. The antenna section 2 applies the microwaves onto the prostate 22, thus heating the prostate 22. The sphincter muscle 23 is also heated since it is located near the prostate 22. The temperatures detected by the temperature sensors 3 and 24 gradually rise. When the temperature of the prostate 22, which is detected by the temperature sensor 3, reaches the target value (39° C.), the output signal of the second comparator 17 falls to the low level. Therefore, the output signal of the temperature control section 8 falls to the low level, and so does the output signal of the microwave-emission control section 11. As a result, the microwave-generating section 12 stops generating microwaves, and the temperature of the prostate 22 gradually decreases.

When the temperature detected by the temperature sensor 3 falls below the target value (39° C.), the output signal of the second comparator 17 rises to the high level. Hence, the output signal of the temperature control section 8 rises to the high level, and so does the output signal of the microwave-emission control section 11. The microwave-generating section 12 starts generating microwaves, which are applied from the antenna section 2 onto the prostate 22. The prostate 22 is heated.

Thus, the microwave-emission control section 11 is turned on every time the temperature of the prostate 22 reaches the target value, and is turned off every time the temperature of the prostate 22 falls below the target value, as shown in FIG. 5, in order to maintain the prostate 22 at the target temperature (39° C.).

When the temperature detected by the first ambient temperature sensor 24, i.e., the temperature in the vicinity of the sphincter muscle 23, rises to or above the second burn temperature (42° C.), or when the temperature detected by the second ambient temperature sensor 25, i.e., the temperature in the rectum 32, rises to or above the third burn temperature (43° C.), the output signal of the microwave-emission interrupting section 31 falls to a low level. This signal is supplied to the microwave-emission control section 11 and also to the alarm-generating section 15. The section 11 turns off the microwave-generating section 12, which stops generating microwaves. At the same time, the section 15 generates a visual or audio alarm, indicating that the temperature in the vicinity of the sphincter muscle 23 has risen above the second burn temperature, or that the temperature in the rectum 32 has risen above the third burn temperature.

In the second embodiment, the microwave-generating section 12 stops generating microwaves the moment the temperature detected by the first ambient temperature sensor 24 rises to or above the second ambient temperature 42° C.), or the moment the temperature detected by the second ambient temperature sensor 25 rises to or above the third burn temperature (43° C.), the output signal of the microwave-emission interrupting section 31 falls to the low level, and the microwave-emission control section 11 causes the microwave-generating section 12 to stop generating microwaves. Instead, the section 12 may be so controlled as to reduce the microwave emission when the temperature detected by the sensor 24 rises to or above the second burn temperature, or when the temperature detected by the sensor 24 rises to or above the third turn temperature.

As described above, the first ambient temperature sensor 24 and the second ambient temperature sensor 25 are provided on and outside the applicator 1, respectively, and the microwave-generating section 12 stops generating microwaves and the alarm-generating section 15 generates a visual or audio alarm, when the temperature detected by the first ambient temperature sensor 24, i.e., the temperature in the vicinity of the sphincter muscle 23, reaches the second burn temperature, or when temperature detected by the second ambient temperature sensor 25, i.e., the temperature of the vicinity of the rectal muscosal membrane, reaches the third burn temperature. Thus, any adjacent part (i.e., the sphincter muscle 23 and the rectal muscosal membrane is protected from burn.

A microwave thermatological device, which is the third embodiment of the invention, will be described below, with reference to FIG. 9.

The third embodiment differs from the first embodiment (FIG. 1) in two respects. First, the first burn-temperature setting section 37 sets the first burn temperature in accordance with the target temperature set by operating the target-temperature setting section 36, not merely by operating the section 10 as in the first embodiment. Secondly, the second burn-temperature setting section 38 sets the second burn temperature in accordance with the target temperature set by operating the section 36, not merely by operating the section 14 as in the first embodiment.

In other respects, the device of the third embodiment is the same as the first embodiment. Those components of the device which are identical or similar to those of the first embodiment are designated at the same reference numerals in FIG. 9 and will not be explained in detail in the following description.

Figure 9:
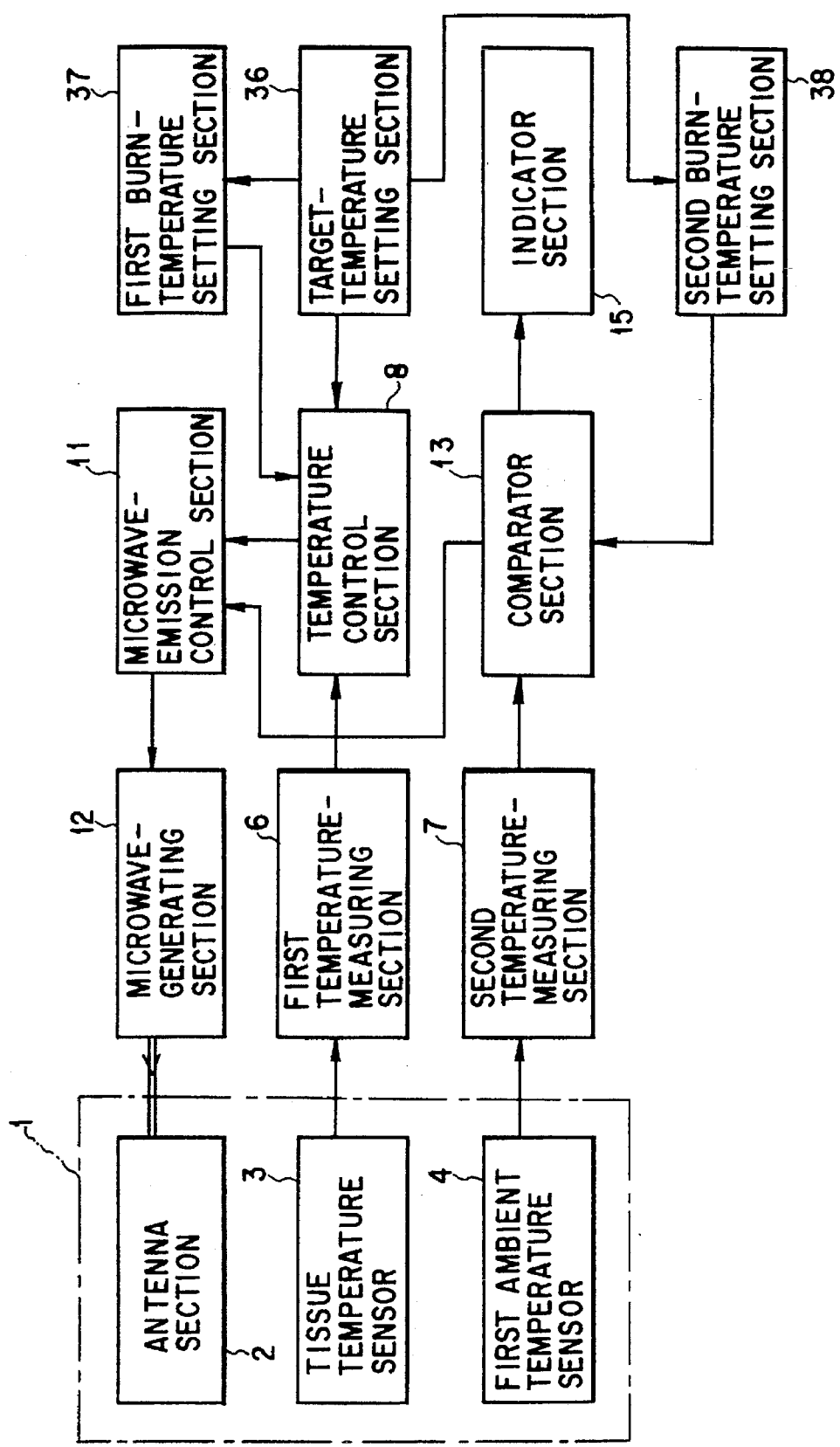
FIG. 9 is a block diagram showing a microwave thermatological device according to a third embodiment of the present invention.

As can be understood from FIG. 9, the target temperature set by operating the target-temperature setting section 36 is input to a temperature control section 8, the first burn-temperature setting section 37 and the second burn-temperature setting section 38. The first burn-temperature setting section 37 sets the first burn temperature in accordance with the target temperature. Similarly, the second burn-temperature setting section 38 sets the second burn temperature in accordance with the target temperature.

Except for this specific method of setting the first and second burn temperatures, the third embodiment operates in the same way as the first embodiment. That is, every time the temperature detected by the temperature sensors 3, i.e., the temperature of the affected part contacting the applicator 1, reaches the target value, the microwave-generating section 12 stops generating microwaves, thus maintaining the affected part at the target temperature. When the temperature detected by the ambient temperature sensor 4, i.e., the temperature in the vicinity of a part adjacent to the affected part, reaches the second burn temperature, the microwave-generating section 12 stops generating microwaves, thereby protecting the adjacent part from burn. Furthermore, the first and second burn temperatures are accurately set since they are automatically set by the burn-temperature setting sections 37 and 38 in accordance with the target temperature set by operating the target-temperature setting section 36.

A microwave thermatological device, which is the fourth embodiment of the present invention, will be described below, with reference to FIGS. 10 to 13.

The fourth embodiment differs from the first embodiment (FIG. 1) in that the first burn-temperature setting section 37 sets the first burn temperature in accordance with the target temperature set by operating the target-temperature setting section 36, not merely by operating the section 10 as in the first embodiment. Except for this point, the device of fourth embodiment is the same as the first embodiment. The second burn temperature is set by operating the second burn-temperature setting section 38, as in the first embodiment. Those components of the device which are identical or similar to those of the first embodiment are designated at the same reference numerals in FIG. 10 and will not be explained in detail in the following description.

As can be understood from FIG. 10, the target temperature set by operating the target-temperature setting section 36 is supplied to a temperature control section 8 and also to the first burn-temperature setting section 37. The section 37 sets the first burn temperature in accordance with the target temperature, such that the first burn temperature has the relationship shown in FIG. 11. The section 37 has a circuit of the type shown in FIG. 12. The circuit comprises two resistors R and R' connected in series between the power source Vcc and the ground, and a capacitor and a resistor connected between the input terminal and the node of the resistors R and R'. The output terminal of the circuit is connected to the node of the resistors R and R'. A voltage Vin corresponding to the target temperature is applied the input terminal, and a voltage Vout corresponding to the first burn temperature is output at the output terminal. These voltages Vin and Vout have the relationship shown in the table of FIG. 13.

In operation, when the target-temperature setting section 36 is operated, setting the target temperature, the first burn-temperature setting section 37 sets the first burn temperature based on the target temperature. Except for this specific method of setting the first burn temperature, the fourth embodiment operates in the same way as the first embodiment.

In the fourth embodiment, the temperature of the affected part is detected by the temperature sensors 3 and is controlled to be equal to the target temperature. Meanwhile, the temperature in the vicinity of a part adjacent to the affected part is detected by the ambient temperature sensor 4 (not shown). When this temperature reaches the second burn temperature, the microwave-generating section 12 stops generating microwaves, thereby protecting the adjacent part from burn. The first burn temperatures is accurately set since it is automatically set by the first burn-temperature setting section 37 in accordance with the target temperature set by operating the target-temperature setting section 36.

In the fourth embodiment, it is the first burn temperature which is automatically set based on the target temperature. Instead, the second burn temperature may be automatically set in accordance with the target temperature. In this case, the first burn-temperature setting section 37 is operated to set the first burn temperature, whereas the second burn-temperature setting section 38 includes the circuit of FIG. 12 and sets the second burn temperature in accordance with the target temperature.

Moreover, in the case where three or more ambient temperature sensor are provided on the applicator 1, the burn temperature to be compared with the temperature detected by one of these sensors may be set in accordance with the target temperature as in the fourth embodiment.

In the embodiments described above, one ambient temperature sensor is located away from the applicator 1. Instead, two or more ambient temperatures can be located far from the applicator 1.

A microwave thermatological device, which is the fifth embodiment of the present invention, will be described below, with reference to FIG. 14.

In the third embodiment (FIG. 9), the first burn-temperature setting section 37 sets the first burn temperature (i.e., the maximum temperature the temperature sensor 3 can detect) in accordance with the target temperature, and the second burn-temperature setting section 38 sets the second burn temperature (i.e., the maximum temperature the ambient temperature sensor 4 can detect) in accordance with the target temperature. In the fifth embodiment, not only the maximum temperatures the sensors 3a and 4a can detect, but also the minimum temperatures these sensors 3a and 4a can detect, are set.

Those components of the fifth embodiment, which are identical or similar to those of the first embodiment, are designated at the same reference numerals in FIG. 14 and will not be explained in detail in the following description.

Figure 14:
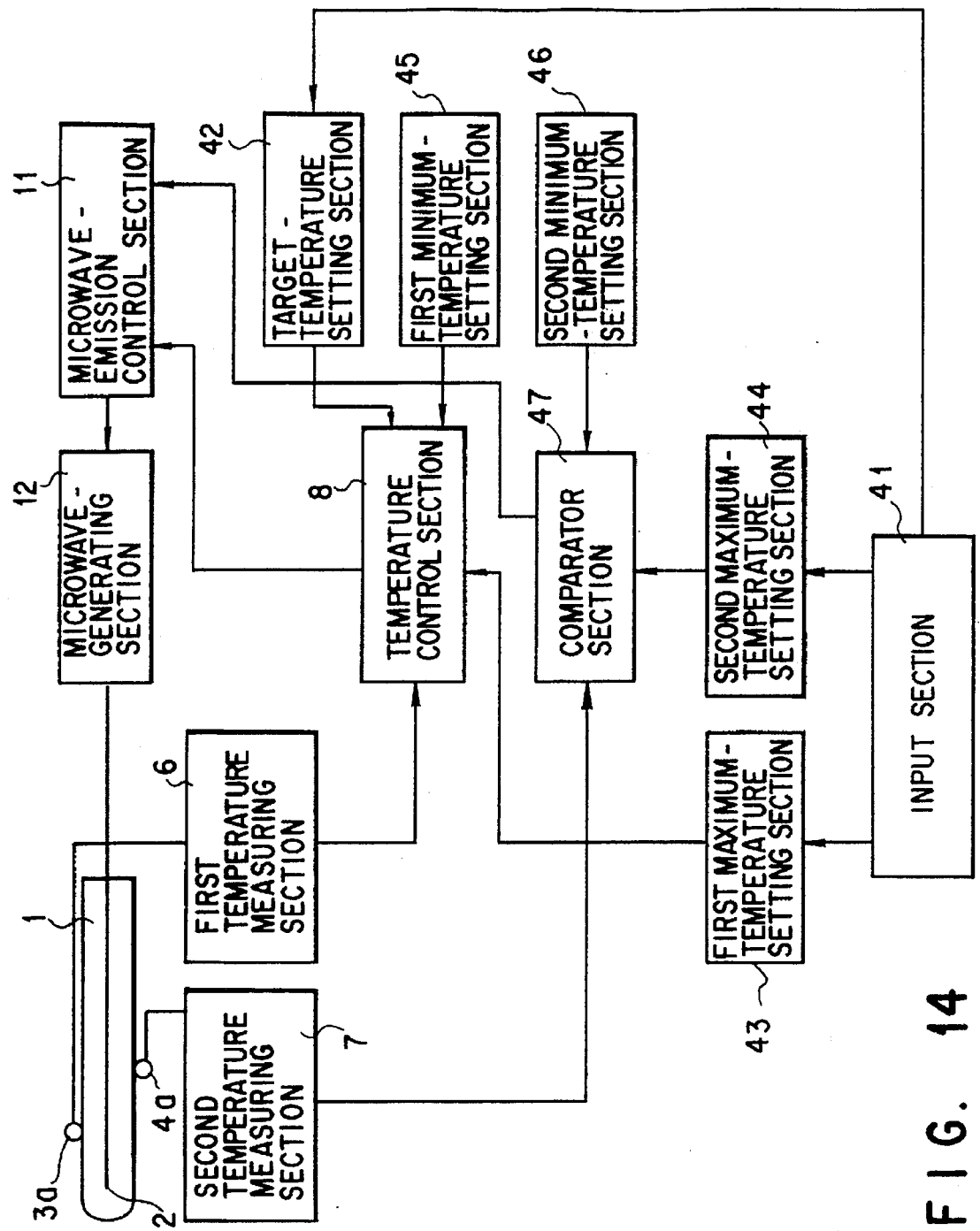
FIG. 14 is a block diagram showing a microwave thermatological device according to a fifth embodiment of the present invention.

As shown in FIG. 14, the first temperature sensor 3a and the second temperature sensor 4a are mounted on the outer circumferential surface of an applicator 1, so that they may contact two parts in a body cavity, respectively, which are adjacent to each other. The device shown in FIG. 14 comprises, besides the applicator 1 and the temperature sensors 3a and 3b, an antenna section 2, two temperature-measuring sections 6 and 7, a temperature control section 8, a microwave-emission control section 11, a microwave-generating section 12, an input section 41, a target-temperature setting section 42, two maximum-temperature setting sections 43 and 44, two minimum-temperature setting sections 45 and 46, and a comparator section 47.

The input section 41 is operated, generating three signals for setting a target temperature, the first maximum temperature and the second maximum temperature. These signals are supplied to the target-temperature setting section 42, the first maximum-temperature setting section 43 and the second maximum-temperature section 44, respectively. The first minimum-temperature setting section 45 is provided for setting the first minimum temperature, and the second minimum-temperature setting section 46 for setting the first minimum temperature.

The temperature control section 8, the microwave-emission control section 11, the microwave-generating section 12, and the antenna 2 operate in the same way as in the first embodiment, in order to maintain the temperature detected by the first temperature sensor 3a at the target temperature set by the target-temperature setting section 42.

The temperature control section 8 supplies a microwave-emission interruption signal to the microwave-emission control section 11, when the temperature detected by the first temperature sensor 3a rises above the first maximum temperature set by the first maximum-temperature setting section 43 or falls below the first minimum temperature set by the first minimum-temperature setting section 45. The comparator section 47 outputs a microwave-emission interruption signal to the microwave-emission control section 11, when the temperature detected by the second temperature sensor 4a rises above the second maximum temperature set by the second maximum-temperature setting section 44 or falls below the second minimum temperature set by the second minimum-temperature setting section 46. The section 11 stops driving the microwave-generating section 12 in response to the microwave-emission interruption signal supplied from the temperature control section 8 or the comparator section 47.

The operation of the device (FIG. 14) according to the fifth embodiment will now be explained.

Upon receipt of a signal at a high level, supplied from the microwave-emission control section 11, the microwave-generating section 12 starts generating microwaves. The antenna section 2 emits the microwaves to the affected part (not shown) which is in contact with the applicator 1, thereby heating the affected part. As a result, the temperatures detected by the temperature sensors 3a and 4b rise gradually.

The control signal supplied from the temperature control section 8 to the microwave-emission control section 11 falls to a low level when the temperature detected by the first temperature sensor 3a reaches the target temperature set by the target-temperature setting section 42, and rises to a high level when the temperature detected by the first temperature sensor 3a reaches the target temperature. The section 11 drives the microwave-generating section 12 while the signal stays at the high level, and do not drive the section 12 while the signal remains at the low level. Hence, the temperature of the affected part is controlled to be equal to the target temperature.

As described above, the temperature control section 8 supplies a microwave-emission interruption signal to the microwave-emission control section 11, when the temperature detected by the first temperature sensor 3a rises above the first maximum temperature set by the section 43 or falls below the first minimum temperature set by the section 45, indicating the possibility that the control section is malfunctioning. Furthermore, the comparator section 47 outputs a microwave-emission interruption signal to the microwave-emission control section 11, when the temperature detected by the second temperature sensor 4a rises above the second maximum temperature set by the section 44 or falls below the second minimum temperature set by the section 46, also indicating the possibility that the control section 8 is malfunctioning. In response to the microwave-emission interruption signal supplied from the temperature control section 8 or the comparator section 47, the microwave-emission control section 11 stops driving the microwave-generating section 12. Therefore, the microwave thermatological device is highly safe.

A microwave thermatological device, which is the sixth embodiment of the present invention, will be described below, with reference to FIG. 15.

In the fifth embodiment described above, the first and second minimum temperatures set by operating the sections 45 and 46 are constants. In the sixth embodiment, the sections 45a and 46b change the first and second minimum temperatures upon receipt of signals output from a timer 48. For instance, the first and second minimum temperatures, both set at 10° C. at the start of the microwave thermatological treatment, are changed to 30° C. upon lapse of 60 seconds from the start of the treatment.

Alternatively, only minimum-temperature setting sections, either the section 45a or the section 46b, may change the minimum temperature upon receipt of a signal supplied from the timer 48. Furthermore, the first minimum temperature and the second minimum temperature may be changed upon lapse of different periods. For example, the section 45a may change the first minimum temperature upon lapse of 60 seconds from the start of the microwave thermatological treatment, whereas the section 45b may change the first minimum temperature upon lapse of 120 seconds from the start of the treatment.

Figure 15:
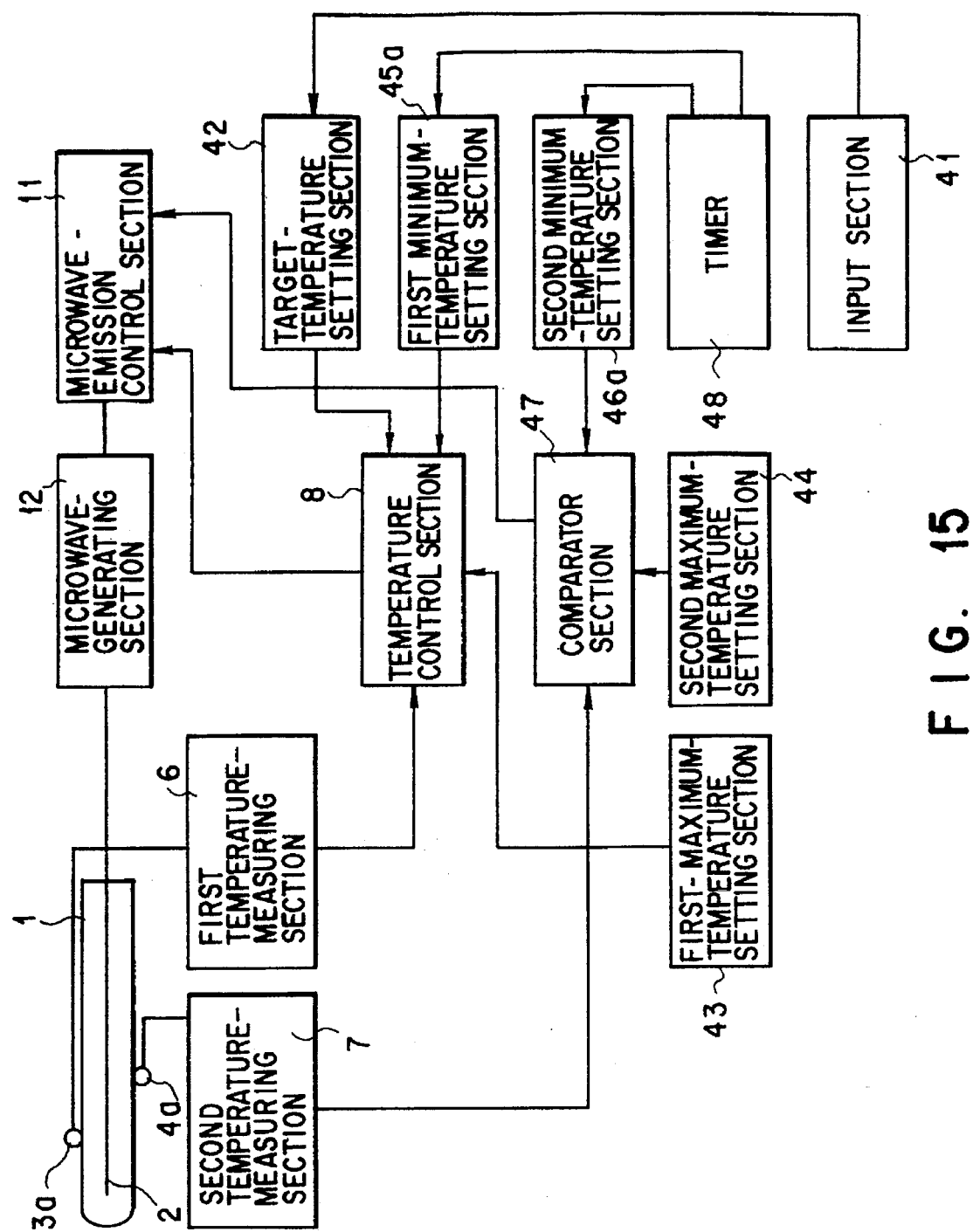
FIG. 15 is a block diagram showing a microwave thermatological device according to a sixth embodiment of the invention.

Except for the above-described changing of the first and second minimum temperatures, the device shown in FIG. 15 operates in the same way as the fifth embodiment (FIG. 14).

As in the fifth embodiment (FIG. 14), the temperature control section 8 supplies a microwave-emission interruption signal to the microwave-emission control section 11, when the temperature detected by the first temperature sensor 3a rises above the first maximum temperature or falls below the first minimum temperature, indicating the possibility that the control section is malfunctioning; and the comparator section 47 outputs a microwave-emission interruption signal to the microwave-emission control section 11, when the temperature detected by the second temperature sensor 4a rises above the second maximum temperature or falls below the second minimum temperature, also indicating the possibility that the control section 8 is malfunctioning. Therefore, the microwave thermatological device according to the sixth embodiment is equally safe.

In the six embodiments described above, the temperature sensor 3 (3a in the fifth and sixth embodiments) detects the temperature of the part undergoing the microwave thermatological treatment. Instead, two temperature sensors may be used to detect the temperature of the part, as will be described with reference to FIGS. 16A, 16B, 17A, 17B, 18A and 18B.

More specifically, as shown in FIGS. 16A and 16B, which are a plan view and a side view of the distal end portion of the applicator 1, two temperature sensors 51 and 52 are mounted on the outer circumferential surface of the applicator 1 and spaced apart by 180° along the circumference of the applicator 1—both aligned in a center line A of the microwave-applied region.

Alternatively, as illustrated in FIGS. 17A and 17B, the temperature sensors 51 and 52 may be mounted on the outer circumferential surface of the applicator 1 and spaced apart by 90° along the circumference of the applicator 1 and aligned in the center line A of the microwave-applied region.

Still alternatively, as shown in FIGS. 18A and 18B, the temperature sensors 51 and 52 may be positioned close to each other on the outer circumferential surface of the applicator 1 and aligned in the center line A of the microwave-applied region.

In the case where two temperature sensors are aligned in the center line A of the microwave-applied region, as shown in FIGS. 16A and 16B, FIGS. 17A and 17B or FIGS. 18A and 18B, the sensors can detect, with accuracy, the temperature of substantially the same portion of a part.

In the six embodiments described above, the temperature sensor 3 (3a in the fifth and sixth embodiments) and the ambient temperature sensor 4 (4a in the fifth and sixth embodiments), both provided on the outer circumferential surface of the applicator 1, can assume one of various positional relationships illustrated in FIGS. 19A and 19B, FIGS. 20A and 20B, FIGS. 21A and 21B, FIGS. 22A and 22B, FIGS. 23A and 23B and FIGS. 24A and 24B.

In the case shown in FIGS. 19A and 19B, the temperature sensor 51 is located in the center line A of a microwave-applied region a, whereas the ambient temperature sensor 52 is located more proximal than the sensor 51, at one side of the region a, and spaced apart by 180° C. along the circumference of the applicator 1. So located, the ambient temperature sensor 52 can reliably monitor the temperature of the part which is to be protected from burn. The ambient temperature sensor 52 may be located more distal, not proximal, than the sensor 51

In the case shown in FIGS. 20A and 20B, the temperature sensor 51 is located in the center line A of a microwave-applied region a, whereas the ambient temperature sensor 52 is located more proximal than the sensor 51, at one side of the region a, and spaced apart by 90° along the circumference of the applicator 1. So located, the ambient temperature sensor 52 can reliably monitor the temperature of the part which is to be protected from burn. The ambient temperature sensor 52 may be located more distal, not more proximal, than the sensor 51.

In the case shown in FIGS. 21A and 21B, the temperature sensor 51 is located in the center line A of a microwave-applied region a, whereas the ambient temperature sensor 52 is located more proximal than the sensor 51, at one side of the region a, and not so much spaced from the temperature sensor 51 long the circumference of the applicator 1. So located, the ambient temperature sensor 52 can reliably monitor the temperature of the part which is to be protected from burn. The ambient temperature sensor 52 may be located more distal, not more proximal, than the sensor 51.

In the case shown in FIGS. 22A and 22B, the temperature sensor 51 is located at the distal side of a microwave-applied region a, whereas the ambient temperature sensor 52 is at the proximal side of the region a and spaced apart by 180° along the circumference of the applicator 1. Alternatively, both temperature sensors 51 and 52 may be placed at the distal side 52a of the region a or at the proximal side 51a of the region a, respectively.

In the case shown in FIGS. 23A and 23B, the temperature sensor 51 is located at the distal side 52a of a microwave-applied region a, whereas the ambient temperature sensor 52 is at the proximal side 51a of the region a and spaced apart by 90° along the circumference of the applicator 1. Alternatively, the temperature sensors 51 and 52 may be placed at the proximal side 51a of the region a or at the distal side 52a of the region a, respectively.

In the case shown in FIGS. 24A and 24B, the temperature sensor 51 is located in the distal side 52a of a microwave-applied region a, whereas the ambient temperature sensor 52 is located at the proximal side 51a of the region a, and not so much spaced from the temperature sensor 51 long the circumference of the applicator 1. Alternatively, the temperature sensors 51 and 52 may be placed at the proximal side 51a of the region a or at the distal side 52a of the region a, respectively.

In the case where a temperature sensor and an ambient temperature sensor are located as shown in FIGS. 19A and 19B, FIGS. 20A and 20B, FIGS. 21A and 21B, FIGS. 22A and 22B, FIGS. 23A and 23B or FIGS. 24A and 24B, these temperature sensors can detect, with accuracy, the temperature of the part being treated and that of an adjacent part, respectively.

An applicator having two temperature sensors will be described, with reference to FIG. 25 which is an exploded perspective view. As shown in FIG. 25, the applicator comprises an insertion section 61 and a sheath 65 in which the section 61 slidably extends. The insertion section 61 contains a microwave-emitting section 63. A balloon 62 is mounted on the distal end of the insertion section 61. The first temperature sensor 64 is mounted on that portion of the section 61 in which the microwave-emitting section 63 is located. The sensor 64 is used to detect the temperature of a part undergoing microwave thermatological treatment. The second temperature sensor 66 is mounted on the distal end portion of the sheath 65, for detecting the temperature of the inner surface of the body cavity into which the applicator is inserted. The temperature sensors 64 and 66 are electrically connected by signal lines 64a and 66a, respectively, to a temperature control section (not shown). The temperature control section comprises all parts of any embodiment described above, except the applicator 1.

How the applicator shown in FIG. 25 is used will be explained. The insertion section 61 is inserted into a body cavity, together with the sheath 65. The balloon 62 is inflated, whereby the section 61 is fixed at a desired position in the body cavity. Then, the sheath 65 is moved, setting the second temperature sensor 66 at a desired position in the body cavity. Thereafter, the microwave-generating section 63 is driven, generating microwaves. The microwaves are applied to an affected part, heating this part. The first temperature sensor 64 detects the temperature of the part being treated, while the second temperature sensor 66 detects the temperature of the inner surface of the body cavity. When the temperature of the part rises to or above a target temperature, the microwave-generating section 72 stops generating microwaves. Hence, the temperature of a part is controlled to be equal to the target temperature.

Since the sheath 65 can be moved back and forth, the second temperature sensor 66 can be moved to any desired position in the body cavity to detect the temperature of any part adjacent to the affected part.

Another applicator, which also has two temperature sensors, will be described with reference to FIG. 26, which is an exploded perspective view. As shown in FIG. 26, this applicator comprises an insertion section 70, a balloon 71 mounted on the distal end portion of the section 70, a microwave-emitting section 72 contained in the section 70, and a first temperature sensor 73 mounted on that portion of the section 70 in which the microwave-emitting section 72 is located. The first temperature sensor 73 is used to detect the temperature of a part undergoing microwave thermatological treatment.

The applicator further comprises a tubular member 74 slidably held in a passage 75 formed in the insertion section 70 and extending parallel to the axis of the section 70. The member 74 can be moved back and forth along the insertion section 70. A second temperature sensor 76 is mounted on the distal end portion of the tubular member 74, for detecting the temperature of the inner surface of the body cavity into which the applicator is inserted.

The temperature sensors 73 and 76 are electrically connected by signal lines 73a and 76a, respectively, to a temperature control section (not shown). The signal lines 73a and 76a extend through the insertion section 70 and the tubular member 75, respectively. The temperature control section comprises all parts of any embodiment described above, except the applicator 1.

How the applicator shown in FIG. 26 is used will be explained. The insertion section 70 is inserted into a body cavity, together with the second temperature sensor 76. The balloon 71 is inflated, whereby the section 70 is fixed at a desired position in the body cavity. Then, the tubular member 74 is moved, setting the second temperature sensor 76 at a desired position in the body cavity. Thereafter, the microwave-generating section 72 is driven, generating microwaves. The microwaves are applied to an affected part, heating this part. The first temperature sensor 73 detects the temperature of the part being treated, while the second temperature sensor 76 detects the temperature of the inner surface of the body cavity. When the temperature of the part rises to or above a target temperature, the microwave-generating section 72 stops generating microwaves. Hence, the temperature of the part is controlled to be equal to the target temperature.

By moving the tubular member 74 along the insertion section 70, the second temperature sensor 76 can be moved to any desired position in the body cavity to detect the temperature of any part adjacent to the affected part.

The device according to the first embodiment of the invention is one designed to perform thermatological treatment on the prostate. Nonetheless, the present invention can be applied to devices for performing thermatological treatment at the rectum, the esophagus and the uterus.

FIG. 27 is a sectional view of the rectum and explains how a device of this invention is used to perform thermatological treatment on the rectum. Shown in FIG. 27 are the device, the rectum 81, the sphincter muscle 82, and an affected part 83 located right above the rectum. The device comprises an applicator 1, a balloon 84 mounted on the distal end portion of the applicator 1, a part temperature sensor 85, and an ambient temperature sensor 86. Both sensors 85 and 86, which correspond to thee sensors 3 and 4 of the first embodiment (FIG. 1), are mounted on the outer circumferential surface of the applicator 1, for detecting the temperature of the affected part 83 and that of the sphincter muscle 82, respectively.

The applicator 1 is inserted into the rectum 81 via the sphincter muscle 82 until its distal end reaches the affected part 83. Then, the balloon 84 is inflated, thereby fixing the applicator 1 in place. Thereafter, thermatological treatment is applied to the affected part 83, while controlling the applicator 1 in accordance with the temperatures detected by the sensors 85 and 86 in the same manner as in the first embodiment.

FIG. 28 is a sectional view showing the esophagus 91, the stomach 92 and the diaphragm 93, and explaining how a device of the present invention is used to perform thermatological treatment in the esophagus 91. Also shown in FIG. 28 are the constricted part 94 of the diaphragm 93, the constricted part 95 of the tracheoaorta, and an affected part 96. The device comprises an applicator 100, a balloon 101 mounted on the distal end portion of the applicator 100, a temperature sensor 102, a first ambient temperature sensor 103 and a second ambient temperature sensor 104. The three sensors 102, 103 and 104, which correspond to the sensors 3, 24 and 25 of the second embodiment (FIG. 7), are mounted on the outer circumferential surface of the applicator 100, for detecting the temperature of the affected part 96, the constricted part 94 of the diaphragm 93 and the tracheoaorta 95, respectively. The device differs from the second embodiment (FIG. 7), in that two ambient temperature sensors 103 and 104, not only one ambient temperature sensor, are mounted on the outer circumferential surface of the applicator 100.

The applicator 100 is inserted into the stomach 92 through the esophagus 91 until its distal end portion is placed in the constricted part 94 of the diaphragm 93, as is illustrated in FIG. 28. Then, the balloon 101 is inflated, thereby fixing the applicator 100 in place, with the sensors 102, 103 and 104 located at the affected part 96, the constricted part 94 of the diaphragm 93 and the tracheoaorta 95, respectively. Thereafter, thermatological treatment is applied to the affected part 96, while controlling the applicator 100 in accordance with the temperatures detected by the sensors 102, 103 and 104 in the same manner as in the second embodiment.

FIG. 29 is a sectional view of the uterus, explaining how the device of this invention is used to perform thermatological treatment in the uterus. Also shown in FIG. 29 are the device, the corpus uteri 110, the neck 111 of the uterus and an affected part 112. The device comprises an applicator 113, a balloon 114 mounted on the distal end portion of the applicator 113, a temperature sensor 115, a first ambient temperature sensor 116 and a second ambient temperature sensor 117. The three sensors 115, 116 and 117, which correspond to the sensors 3, 24 and 25 of the second embodiment (FIG. 7), are mounted on the outer circumferential surface of the applicator 113, for detecting the temperature of the affected part 112, the neck 111 of the uterus and the entrance to the corpus uteri 110, respectively. The device differs from the second embodiment (FIG. 7), in that two ambient temperature sensors 116 and 117, not only one ambient temperature sensor, are mounted on the outer circumferential surface of the applicator 113.

The applicator 113 is inserted into the corpus uteri 110 through the neck 111 of the uterus until its distal end portions enters the corpus uteri 110, as is illustrated in FIG. 29. Then, the balloon 114 is inflated, thereby fixing the applicator 113 in place, with the sensors 115, 116 and 117 located at the affected part 112, the neck 111 of the uterus and the entrance to the corpus uteri 110, respectively. Thereafter, thermatological treatment is applied to the affected part 112, while controlling the applicator 113 in accordance with the temperatures detected by the sensors 115, 116 and 117 in the same way as in the second embodiment.

A hyperthermia device, which is the seventh embodiment of the invention, will be described with reference to FIG. 30 which is a block diagram.

Figure 30:
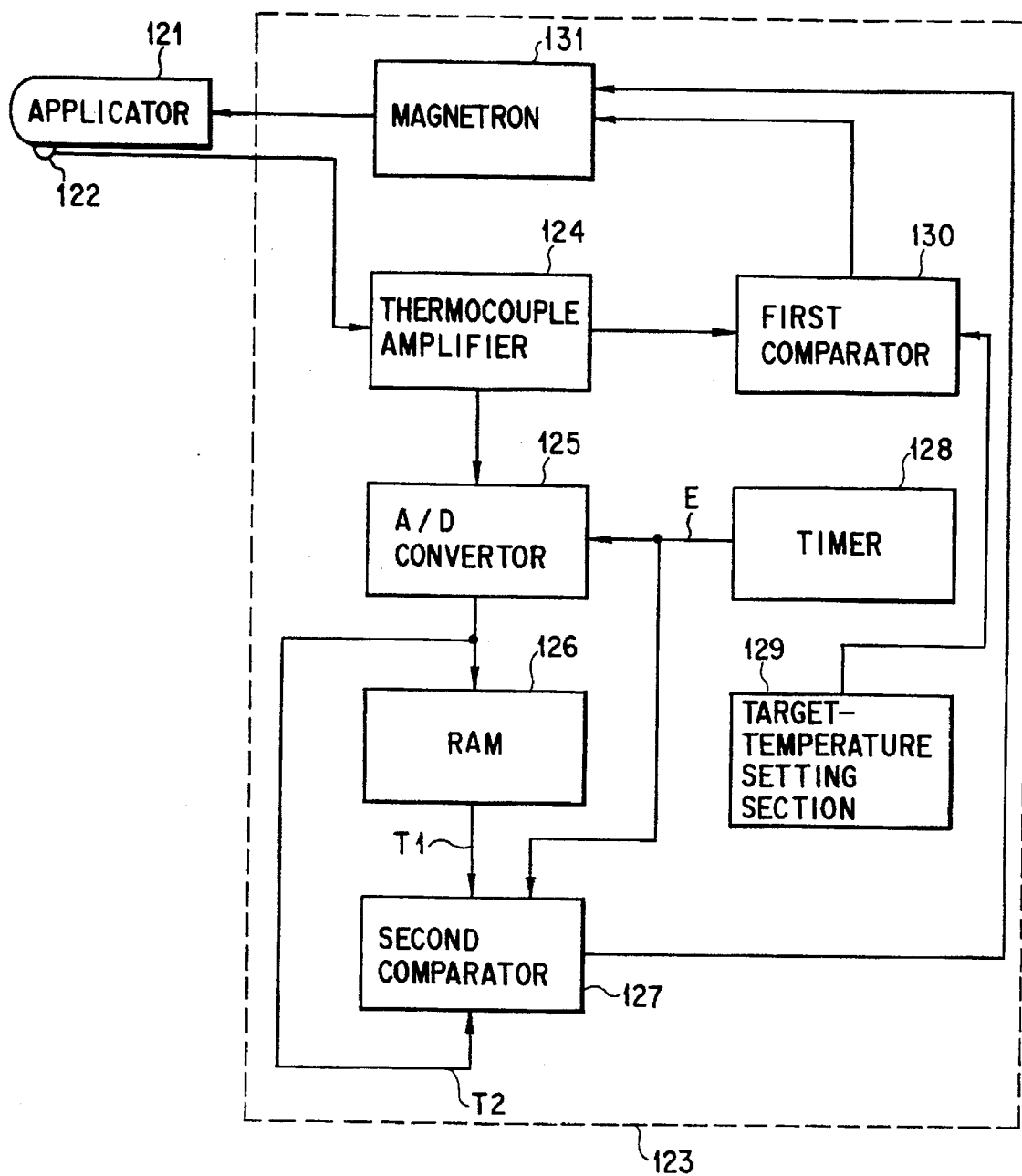
FIG. 30 is a block diagram showing a hyperthermia device which is a seventh embodiment of the present invention.

As shown in FIG. 30, the hyperthermia device comprises an applicator 121, a thermocouple 122, and a main section 123. The applicator 121 is designed to apply microwaves to an affected part. The main section 123 contains a thermocouple amplifier 124, an A/D converter 125, a RAM 126, a first comparator 130, a second comparator 127, a timer 128, a target-temperature setting section 129, and a magnetron 131.

The thermocouple 122 is mounted on the distal end portion of the applicator 121, for detecting the temperature of an affected part and generates a signal representing this temperature. The thermocouple 122 is electrically connected to the thermocouple amplifier 124, which amplifies the signal generated by the thermocouple 122. The thermocouple amplifier 124 has such an amplification factor that its output voltage is 0.1× (temperature of the part) [V]. Thus, if the temperature of the affected part is 40° C., the output voltage of the amplifier 124 will be 4 V (=0.1×40).

The voltage signal output by the amplifier 124 is input to the A/D converter 125. The A/D converter 125 converts the signal to a digital voltage signal, which is supplied to the RAM 126 and the second comparator 127.

The timer 125 supplies an enable signal E to the A/D converter 125 and the second comparator 127 when the applicator 121 starts applying microwaves to the affected part. Also does it supply n enable signal E to the A/D converter 125 and the second comparator 127 upon lapse of a predetermined period (e.g., 1 minute) from the start of the microwave application. In response to the enable signal E, the A/D converter 125 converts the output voltage of the amplifier 124 to a digital voltage signal and outputs this signal to the RAM 126 and the second comparator 127. In response to the enable signal E, the second comparator 127 compares the voltage T2 represented by the digital signal with the voltage T1 stored in the RAM 126 and representing the temperature which the affected part had a minute ago. The second comparator 127 generates a logic signal. The logic signal is at a high level if T2>T1+ε (e.g., a margin of 0.3 corresponding to 3° C.), indicating that the part is being heated appropriately. It is at a low level if T2≦T1+ε, indicating that the part is being heated improperly. The logic signal is supplied to the magnetron 131.

The target-temperature setting section 129 is operated to set a target temperature. It generates a voltage which is 0.1× (target temperature) [V]. The output voltage of the section 129 is applied to the first comparator 130. Also applied to the first comparator 130 is the output voltage of the thermocouple amplifier 124. The first comparator 130 compares the input voltages and generates a logic signal. This logic signal is at the high level if the output voltage of the section 129 (i.e., the target temperature) is higher than or equal to the output voltage (i.e., the temperature of the part) of the amplifier 124, and at the low level if the output voltage of the section 129 is lower than the output voltage of the amplifier 124. The logic signal output by the first comparator 130 is input to the magnetron 131.

The magnetron 131 generates the logic product of the logic signals supplied from the comparators 127 and 130. The magnetron 131 generates microwaves if the logic product is "1," and stops generating microwaves if the logic product is "0." The microwaves are supplied to the applicator 121.

The operation of the seventh embodiment will be explained.

First, the target-temperature setting section 129 is operated, setting a target temperature to which the affected part is to be heated. Then, the timer 128 starts measuring time and supplies an enable signal E to the A/D converter 125 and the second comparator 127. At the same time, the magnetron 131 is driven, generating microwaves. The applicator 121 applies the microwaves to the affected part, thereby heating the part. The thermocouple 121 detects the temperature of the part being heated, generating a voltage. The thermocouple amplifier 124 amplifies the voltage, which is input to the A/D converter 125. Receiving the enable signal E, the A/D converter 125 converts the voltage into a digital voltage T1. The voltage T1, representing the temperature which the affected part has at the start of the microwave application, is stored into the RAM 126.

The voltage amplified by the amplifier 124, which represents the temperature of the affected part, is applied to the first comparator 130, to which the output voltage of the section 129 is applied as well. The first comparator 130 compares these input voltages. It generates a logic signal at the high level if the output voltage of the section 129 (i.e., the target temperature) is higher than or equal to the output voltage of the amplifier 124 (the temperature of the part), and a signal at the low level if the output voltage of the section 129 is lower than the output voltage of the amplifier 124. The logic signal is supplied from the first comparator 130 to the magnetron 131 via a voltage control section 147. The magnetron 131 generates microwaves in response to the logic signal at the high level, and stops microwaves in response to the logic signal at the low level. In other words, the magnetron 131 generates microwaves and stops generating them, so as to maintain the affected part at the target temperature set by operating the target-temperature setting section 129.

Upon lapse of a predetermined period (e.g., 1 minute) from the start of the microwave application, the timer 128 supplies an enable signal E to the A/D converter 125 and the second comparator 127. In response to the enable signal E, the A/D converter 125 converts the output voltage of the amplifier 124 to a digital voltage T2. The voltage T2, which represents the temperature which the affected part has 1 minute after the start of the microwave application, is output to the RAM 126 and the second comparator 127. In response to the enable signal E, the second comparator 127 compares the voltage T2 with the voltage T1+ε (i.e. a margin of 0.3 corresponding to 3° C.) stored in the RAM 126 and representing the temperature which the affected part had a minute ago.

The voltage T2 must be higher than the voltage T1+ε if the affected part has been heated sufficiently and if the thermocouple 122 contacts the part. On the other hand, the voltage T2 is equal to or lower than the voltage T1+ε if the thermocouple 122 is displaced from the affected part or short-circuited, or if the applicator 121 happens to be disconnected from the magnetron 131.

If T2>T1+ε (e.g., 3° C.), indicating that the part is being heated appropriately, the second comparator 127 generates a logic signal at the high level, which is input to the magnetron 131. The magnetron 131 continues to generate microwaves and supply them to the applicator 121, whereby the hyperthermia is continued.

If T2≦T1+ε, indicating that the part is being heated improperly, the second comparator 127 generates a logic signal at the low level, which is input to the magnetron 131. The magnetron 131 stops generating microwaves, supplying no microwaves to the applicator 121. The hyperthermia is thereby interrupted.

Furthermore, temperature of the affected part of has risen at a rate lower than a predetermined rate, the magnetron 131 may be stopped so that microwaves are not applied to the affected portion.

As indicated above, whether the heating system and the temperature-detecting system are function well or not is determined from the difference between the temperature the affected part has at present and the temperature the part had one minute ago. Hence, the seventh embodiment is a highly safe hyperthermia device.

A hyperthermia device, which is the eighth embodiment of this invention, will be described with reference to FIG. 31. This device differs from the hyperthermia device according to the seventh embodiment, in that the temperature of an affected part is compared not only with the temperature it had at the start of microwave application, upon lapse of a predetermined period (e.g., 1 minute) from the start of the microwave application, but also with the temperature it had at the interruption of microwave application, upon lapse of a predetermined period (e.g., 1 minute) from the interruption of the microwave application.

Those components of the eighth embodiment, which are identical or similar to those of the seventh embodiment (FIG. 30), are designated at the same reference numerals in FIG. 31 and will not be explained in detail in the following description.

Figure 31:
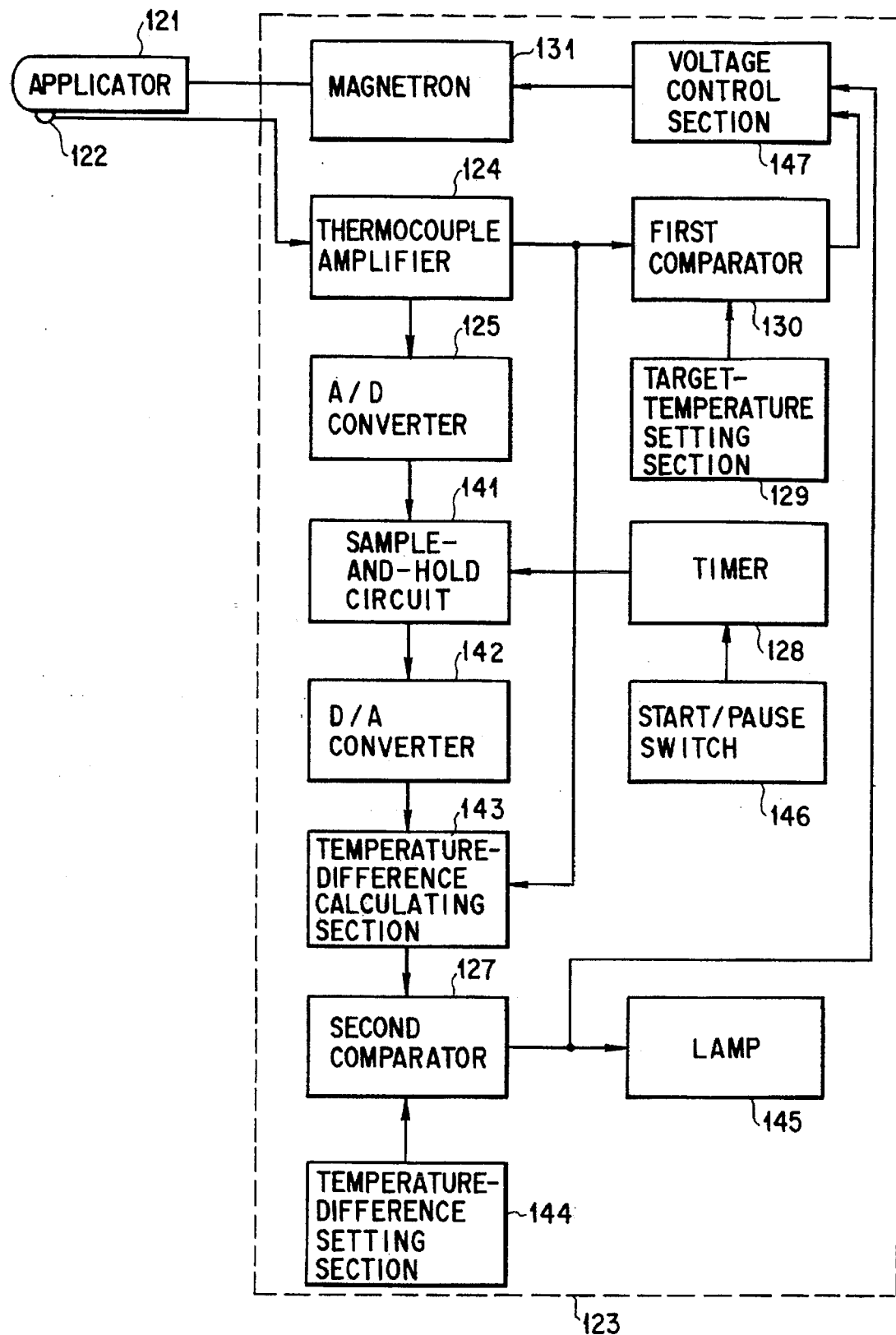
FIG. 31 is a block diagram illustrating a microwave thermatological device according to an eighth embodiment of this present invention.

As can be understood from FIG. 31, the A/D converter 125 is provided for converting the output voltage of the thermocouple amplifier 124 to a digital voltage, which is input to a sample-and-hold circuit 141. The sample-and-hold circuit 141 is used to hold the voltage which the A/D converter 125 outputs when the microwave application is started, and also to hole the voltage which the A/D converter 125 outputs when the microwave-application is interrupted. The timer 128 is so set as to generate a signal upon lapse of the predetermined time (i.e., 1 minute) from the start of the microwave application, and also upon lapse of the predetermined time (i.e., 1 minute) from the interruption of the microwave application. The output of the timer 128 is connected to the sample-and-hold circuit 141.

The output of the sample-and-hold circuit 141 is connected to a D/A converter 142, whose output is connected to a temperature-difference calculating section 143. Connected to the section 143 is the output of the thermocouple amplifier 124. Thus, the section 143 can calculate a difference between the temperature which the affected part had at the start of microwave application and the temperature the part has upon lapse of the predetermined time from the start of microwave application. Also can the section 143 calculate a difference between the temperature which the affected part had at the interruption of microwave application and the temperature of the part has upon lapse of the predetermined time from the interruption of microwave application.

The output of the temperature-difference calculating section 143 is connected to one of the two inputs of the second comparator 117. Connected to the other input of the second comparator 127 is the output of a temperature-difference setting section 144. The section 144 has been operated, setting a temperature difference of less than 7° C. (=43° C.–36° C.). This is because an affected part is heated from about 36° C., i.e., the patient's temperature, to a target temperature of 43° C. when microwaves are applied to the part for the predetermined time of 1 minute. It is desirable that some margin be imparted to the temperature difference. Preferably, the temperature difference is set at 2 to 4° C. In this embodiment, the temperature difference is set at 4° C.

The second comparator 127 compares the output from the section 143 with the output from the temperature difference set by operating the section 144. The second comparator 127 generates a logic signal at the high level if the temperature difference calculated by the section 143 is equal to or greater than the temperature difference set by operating the section 144. The high-level logic signal indicates that the affected part is being heated appropriately. The second comparator 127 generates a logic signal at the low level if the temperature difference calculated by the section 143 is less than the temperature difference set by operating the section 144. The low-level logic signal indicates that the part is not being properly heated, possibly due to the disconnection of the applicator 121 to the magnetron 131, the malfunction of the thermocouple 122 or the displacement of the thermocouple 122 from the affected part.

The output of the second comparator 127 is connected to a lamp 145 and the voltage control section 147. The lamp 145 will emit light if the output signal of the second comparator 127 is at a low level, thereby informing of a possible trouble with the applicator 121 and/or the thermocouple 122. The voltage control section 147 generates a logic product of the logic signal output from the second comparator 127 with the logic signal output from the first comparator 130. The section 147 outputs a high-level signal to the magnetron 131 if the logic product is "1," and a low-level signal thereto if the logic product is "0." The magnetron 131 starts generating microwaves in response to the high-level signal, and stops generating microwaves in response to the low-level signal.

The operation of the eighth embodiment will be explained.

The voltage control section 147 controls the magnetron 131 in accordance with the logic signal supplied from the first comparator 130, thereby to maintain the affected part at the target temperature set by operating the target-temperature setting section 129.

The magnetron 131 is also controlled, as follows, based on the temperature difference calculated by the section 143. First, a start/pause switch 146 is pushed to start the microwave application to the affected part. The signal which the thermocouple 122 generates at this time and which represents the temperature of the part is amplified by the thermocouple amplifier 124 and converted to a digital voltage by the A/D converter 125. The sample-and-hold circuit 141 holds the digital voltage. Upon lapse of one minute from the start of the microwave application, the timer 128 outputs a signal. In response to this signal the sample-and-hold circuit 141 inputs the voltage to the D/A converter 142. The D/A converter 142 converts the voltage to an analog voltage, which is input to the temperature-difference calculating section 143 which receives the output of the thermocouple amplifier 124, too. The section 143 therefore calculates a difference between the temperature which the affected part had at the start of microwave application and the temperature the part has upon lapse of one minute from the start of microwave application. The section 143 outputs a signal representing this temperature difference, to the second comparator 127.

The second comparator 127 compares the output from the section 143 with the output from the temperature difference set by operating the section 144. The second comparator 127 generates a high-level logic signal if the temperature difference is equal to or greater than 4° C. (i.e., the temperature difference set by operating the section 144), indicating that the affected part is being heated appropriately. The high-level signal is supplied to the lamp 145 and the voltage control section 147. The lamp 145 emits no light. In response to the high-level signal, the voltage control section 147 generates and supplies a high-level logic signal to the magnetron 131. Driven by the high-level logic signal, the magnetron 131 generates microwaves, continuing the microwave treatment on the affected part.

On the other hand, if the temperature difference is less than 4° C., the second comparator 127 generates a low-level logic signal which indicates that the part is not being properly heated, possibly due to the disconnection of the applicator 121 to the magnetron 131, the malfunction of the thermocouple 122 or the displacement of the thermocouple 122 from the affected part. The low-level signal is supplied to the lamp 145 and the voltage control section 147. The lamp 145 emits light in response to the low-level signal output from the second comparator 127, informing of a possible trouble with the applicator 121 and/or the thermocouple 122. Upon receipt of the low-level signal from the second comparator 127, the voltage control section 147 generates a low-level logic signal and supplies it to the magnetron 131. The magnetron 131 stops generating microwaves, interrupting the microwave treatment on the affected part.

Even after the microwave application has been stopped, the treatment can be performed gain. First, the start/pause switch 146 is pushed, thereby causing the timer 128 to stop measuring time. Then, the switch 146 is pushed again, causing the timer 128 to start measuring time. The signal generated at this time by the thermocouple 122 and representing the temperature of the part is amplified and converted to a digital voltage signal. The voltage signal is held by the sample-and-hold circuit 141. Upon lapse of one minute from the start of the microwave application, the voltage signal is compared with the signal which the thermocouple amplifier 124 has Just produced. The difference in magnitude between these signals is a difference between the temperature which the affected part had at the start of microwave application and the temperature the part has upon lapse of one minute from the start of microwave application. Thereafter, the same sequence of operations is carried out as in the initial phase of microwave application.

In the eighth embodiment, the temperature-difference setting section 144 may be operated after the interruption of the microwave application to set a temperature difference different from the initial temperature difference which has been set at the start of microwave application. To be more specific, the temperature difference may be set at a value less than 4° C., for example 2° C. This is because the affected part is not likely to be cooled to the patient's temperature (about 36° C.) during the interruption of microwave application.

As described above, the temperature of the affected part is monitored, not only from the start of the initial microwave application, but also after an interruption of the microwave application, thereby determining whether or not the part is being heated appropriately. Hence, with the eighth embodiment it is possible to perform microwave treatment on the part in safely.

A hyperthermia device, which is the ninth embodiment of the present invention, will now be described with reference to FIG. 32 which is a block diagram.

As shown in FIG. 32, this device comprises two applicators 151a and 151b and a main section 153. The applicators 151a and 151b, both electrically connected to the main section 153, will be placed, opposing each other, in a body cavity in which an affected part is present. The main section 153 contains a temperature-measuring section 154, a voltage comparator 155, a voltage memory section 156, a target-temperature setting section 157, a high-frequency wave generator 158, a cooling water tank 159, a pump 159a, and a power supply section 160.

A temperature-measuring element 152a made of, for example, platinum is mounted on the second applicator 151b, for detecting the temperature of the affected part. The element 152a is electrically connected to the temperature-measuring section 154. The section 154 has such an amplification factor that its output voltage is 0.1× (temperature of the part) [V]. Thus, if the temperature of the affected part is 40° C., the output voltage of the section 154 will be 4 V (=0.1×40). The output voltage of the temperature-measuring section 154 is input to the voltage comparator 155 and the voltage memory section 156. Also input to the voltage comparator 155 is the output voltage of the target-temperature setting section 157, which represents the target temperature set by operating the section 157. The voltage comparator 155 compares the two voltages input to it and generates a logic signal. This signal is at the high level if the output voltage of the section 154 (i.e., the temperature of the affected part) is lower than or equal to the output voltage of the section 157 (i.e., the target temperature), and at the low level if the output voltage of the section 154 is higher than the output voltage of the section 157. The logic signal output by the voltage comparator 155 is input to the high-frequency wave generator 158. The target-temperature setting section 157 is designed to output a voltage which is 0.1× (target temperature) [V].

The high-frequency wave generator 158 is provided to generate high-frequency waves in response to a high-level logic signal from the voltage comparator 155, and to stops generating high-frequency waves in response to a low-level logic signal from the voltage comparator 155. The generator 158 is connected to both applicators 151a and 151b, so that the high-frequency waves may be supplied to the applicators 151a and 151b.

The logic signal output from the voltage comparator 155 is input also to the voltage memory section 156. The memory section 156 stores two voltages T1 and T2. The voltage T1 is output by the temperature-measuring section 154 when the logic signal from the voltage comparator 144 falls from the high level to the low level. The voltage T2 is output by the section 154 when the logic signal from the voltage comparator 144 rises from the low level to the high level. The temperature of the part is somewhat higher while the high-frequency wave generator 158 is generating microwaves than while the generator 158 is not generating microwaves. The voltage memory section 156 generates a signal, which is input to the power supply section 160. This signal is at the high level if If T1−T2≧ε, indicating that the heating system is operating well, and is at the low level if T1−T2<ε, indicating that the heating system or the temperature-measuring system is malfunctioning.

The power supply section 160 is provided to supply electric power to the other components of the main section 153. It supplies power to the other components in response to a high-level signal from the voltage memory section 156, and stop supplying power to them.

The pump 159a is used to supply cooling water from the cooling water tank 159 to the applicators 151a and 151b and vice versa, thereby to circulate the cooling water in each applicator.

The operation of the ninth embodiment, described above, will now be explained.

The temperature-measuring element 152a detects the temperature of an affected part and generates a signal. The temperature-measuring section 154 amplifies the signal into a voltage, which is applied to one of the two input terminals of the voltage comparator 155. The voltage comparator 155 generates a high-level logic signal if the temperature of the part is lower than or equal to the target temperature set by operating the section 157. It generates a low-level logic signal if the temperature of the part is higher than the target temperature. The logic signal output by the voltage comparator 155 is input to the high-frequency wave generator 158. The high-frequency wave generator 158 starts generating high-frequency waves in response to a high-level logic signal, and stops generating the high-frequency waves in response to a low-level logic signal. Thus, the heating of the affected part is controlled so that the part may be heated to the target temperature.

Meanwhile, the output signal of the voltage comparator 155 is supplied to the voltage memory section 156. The section 156 stores the voltage T1 which the temperature-measuring section 154 outputs when the logic signal from the voltage comparator 144 falls from the high level to the low level, and also the voltage T2 which the section 154 outputs when the logic signal from the voltage comparator 144 rises from the low level to the high level. The section 156 generates a signal. This signal is at the high level if If T1−T2≧ε, indicating that the heating system is operating well, and is at the low level if T1−T2<ε, indicating that the heating system or the temperature-measuring system is malfunctioning. The signal is input to the power supply section 160.

In response to the signal at the low level, indicating that the difference between T1 and T2 is relatively small (T1−T2<ε) and that the heating system or the temperature-measuring system is malfunctioning, the power supply section 160 stops supplying electric power to the other components of the main section 153.

In the ninth embodiment, the difference between the temperatures T1 and T2 can be monitored every time the part is heated, thereby determining whether the heating system and the temperature-measuring system are operating well nor not.

Still another hyperthermia device, which is a tenth embodiment of the invention, will be described with reference to FIG. 33 which is a block diagram.

This device differs from the seventh embodiment (FIG. 30), in that the heating system and the temperature-measuring system are examined not only based on the difference between the temperature detected at the start of the initial heating and the temperature detected one minute later, but also based on the difference between the temperature detected at the second heating and the temperature detected one minute later.

Those components of the tenth embodiment, which are identical or similar to those of the seventh embodiment (FIG. 30), are designated at the same reference numerals in FIG. 33 and will not be explained in detail in the following description.

As shown in FIG. 33, a check switch 146 is connected to the timer 128. When operated, the switch 146 will generate a signal, which is supplied to the timer 128 and clears the count value of the timer 128. The output of the second comparator 127 is connected to the magnetron 131 and a lamp 145.

The tenth embodiment heats an affected part in the same way as the seventh embodiment. Unlike in the seventh embodiment, it is possible to check the difference between the temperature detected at any time the check switch 146 is operated and the temperature detected one minute later. In other words, since the count value of the timer 128 is cleared whenever the check switch 146 is pushed, it can be determined how the temperature of the part changes one minute later. Suppose that the applicator 121 is displaced from the affected part during the initial heating of the part. In this case, the initial heating is terminated, and the applicator 121 is moved and placed at an appropriate position. To place the applicator 121 so it usually takes several minutes, during which period the temperature of the affected part falls. To heat the part again, the check switch 146 is pushed, clearing the count value of the timer 128 and resetting the timer 128. The second comparator 127 compares the temperature the detected at the time of operating the switch 146 with the temperature detected upon lapse of one minute, determining how much the temperature of the part has increased. If the temperature increase is relatively small, for example 2° C. or less, the second comparator 127 generates a low-level signal, indicating that the heating system or the temperature-measuring system may be malfunctioning. The low-level signal is supplied to the magnetron 131 and the lamp 145. In response to this signal, the magnetron 131 stops generating microwaves and the lamp 145 emits light, informing the operator that the heating system or the temperature-measuring system may be malfunctioning.

Namely, the heating system and the temperature-measuring system are checked for their function, not only one minute after the start of the initial heating, but also one minute after the second heating.

Figure 34:
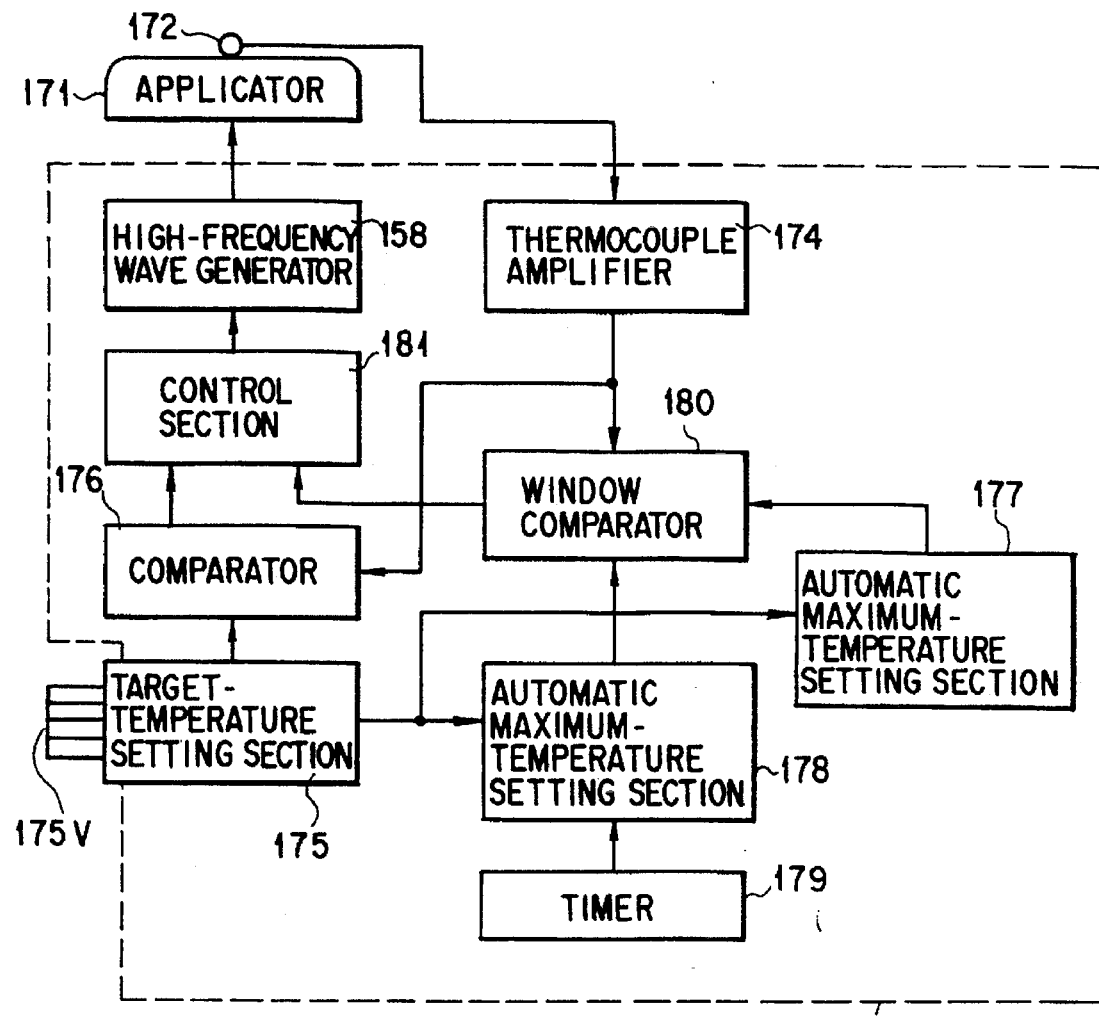
FIG. 34 is a block diagram showing still another hyperthermia device which is an eleventh embodiment of the invention.
Figure 35:
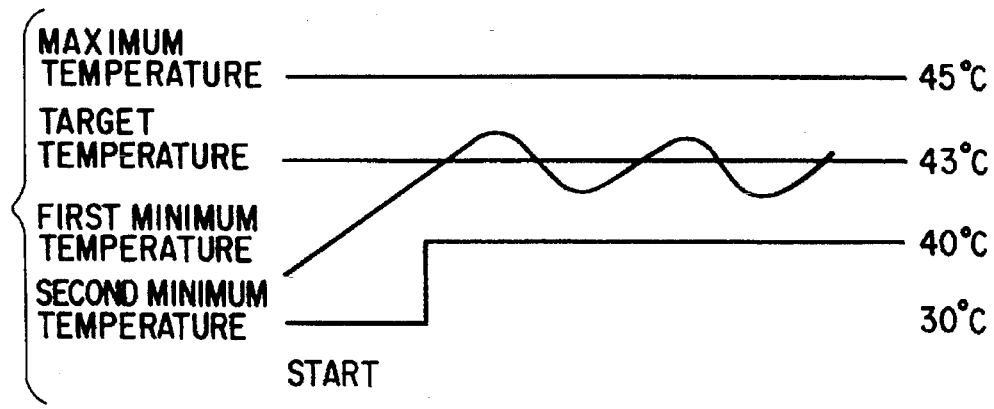
FIG. 35 is a timing chart indicating how the temperature of an affected part changes as the part receives treatment performed by means of the hyperthermia device shown in FIG. 34.

Another hyperthermia device, which is the eleventh embodiment of the present invention, will be described with reference to FIGS. 34 and 35. FIG. 34 is a block diagram, and FIG. 35 is a timing chart showing how the temperature of an affected part changes.

The eleventh embodiment is characterized in that the application of high-frequency waves is stopped when the temperature of the affected part falls outside a range, thereby interrupting the heating of the part. The lower limit of the temperature range, or the minimum temperature, is set at the second value (2) at the start of the heating and set, one minute later, at the first value (1) greater than the second value (2), as is illustrated in the timing chart of FIG. 35.

As shown in FIG. 34, the device comprises an applicator 171, a thermocouple 172 and a main section 173. The main section 173 contains a high-frequency wave generator 158, a thermocouple amplifier 174, a target-temperature setting section 175, a comparator 176, an automatic maximum-temperature setting section 177, an automatic minimum-temperature setting section 178, a timer 179, a window comparator 180, and a control section 181.

The thermocouple 172 is mounted on the applicator 171, for detecting the temperature of an affected part. Its output is connected to the thermocouple amplifier 174. The output of the amplifier 174 is connected to one of the two inputs of the comparator 176 and also to the first of the three inputs of the window comparator 180. The thermocouple amplifier 174 has such an amplification factor that its output voltage is 0.1× (temperature of the part) [V]. Thus, if the temperature of the affected part is 40° C., the output voltage of the amplifier 174 will be 4 V (=0.1×40).

The other input of the comparator 176 is connected to the output of the target-temperature setting section 175. The section 175 has a dial 175 V, which is rotated to set a target temperature. The target-temperature setting section 175 is designed to output a voltage which corresponds to one tenth of the target temperature (=0.1× the target temperature [V]). The output of the section 175 is connected to the comparator 176, the automatic maximum-temperature setting section 177, and the automatic minimum-temperature setting section 178. Also connected to the automatic maximum-temperature setting section 177 is the timer 179 for generating a signal upon lapse of a predetermined time, e.g., one minute, from the time the applicator 171 starts applying high-frequency waves to the affected part.

The automatic maximum-temperature setting section 177 is designed to automatically set a maximum temperature in accordance with the voltage output by the section 175 and corresponding to the target temperature. The output of the section 177 is connected to the second input of the window comparator 180.

The automatic minimum-temperature setting section 178 is designed to automatically set a minimum temperature in accordance with the voltage output by the section 175 and corresponding to the target temperature. Stated more precisely, as shown in FIG. 35, the section 178 set the second minimum temperature (2) when the heating of the part is started, and sets the first minimum temperature (1) higher than the second minimum temperature (2), upon lapse of one minute from the start of the heating. The output of the minimum-temperature setting section 178 is connected to the third input of the window comparator 180.

The target temperature is 43° C., the maximum temperature is 45° C., the first minimum temperature is 40° C., and the second minimum temperature is 30° C.

The comparator 176 is designed to output a logic signal. The logic signal is at the high level if the temperature of the part is equal to or lower than the target temperature, and at the low level if the temperature of the part is higher than the target temperature. The output of the comparator 176 is connected to one of the two inputs of the control section 181.

The other input of the control section 181 is connected to the output of the window comparator 180. The window comparator 180 is designed to generate a logic signal. This logic signal is at the high level if the temperature of the part falls within a range the lower limit of which is the first or second minimum temperature and the upper limit of which is the maximum temperature, and at the low level if the temperature of the part falls outside that range.

The control section 181 is designed to generate a logic product of the logic signals output from the comparator 176 and the window comparator 180, and to produce a drive signal. The drive signal is at a high level if the logic product is "1" and at a low level if the logic product is "0." The output of the control section 181 is connected to the high-frequency wave generator 158.

The high-frequency wave generator 158 starts generating high-frequency waves in response to the high-level drive signal, and stops generating high-frequency waves in response to the low-level drive signal. The generator 158 is connected to the applicator 171, which can apply the waves to the affected part.

The operation of the eleventh embodiment will described below, with reference to the timing chart of FIG. 35.

First, the dial 175 V of the target-temperature setting section 175 is rotated, setting a target temperature. A signal representing the target temperature is input to the comparator 176. The thermocouple 172 detects the temperature of the part, and the amplifier 174 generates a signal representing the temperature detected. This signal is input to the comparator 176. The comparator 176 compares the temperature of the part with the target temperature and generates a signal which is at the high level or the low level, depending on the difference between the temperature compared. The signal the comparator 176 generates is input to the control section 181, which supplies a high-level or low-level signal to the high-frequency wave generator 158. Upon receipt of the signal the generator 158 starts or stops generating high-frequency waves. The temperature of the affected part is thereby controlled to become equal to the target temperature set by operating the target-temperature setting section 175.

Before the application of microwaves, the affected part has a temperature nearly equal to 36° C., i.e., the patient's temperature. Some time after the application of microwaves has been started, the temperature of the part repeatedly rises above and falls below the target temperature, as illustrated in FIG. 35. This is because the control section 181 outputs a high-level signal to the high-frequency wave generator 158 every time the temperature of the part falls below the target temperature, and outputs a low-level signal to the generator 158 every time the temperature of the part rises above the target temperature.

Should the thermocouple 172 malfunction or be disconnected from the high-frequency wave generator 158, the generator 158 would keeps supplying the high-frequency waves to the applicator 171. Consequently, the temperature of the affected part would rise far above the target temperature and even above the maximum temperature (45° C.). The moment the temperature represented by the output voltage of the amplifier 174 raises above the maximum temperature, the window comparator 180 supplies a low-level logic signal to the control section 181. In response to the low-level logic signal, the control section 181 supplies a low-level drive signal to the high-frequency wave generator 158. The generator 158 stops supplying the high-frequency waves to the applicator 171, whereby the temperature of the part starts falling.

Should the output voltage of the thermocouple amplifier 174 fall below the first minimum temperature (40° C.), it is determined that the thermocouple 172 is short-circuited, that the high-frequency wave generator 158 fails to generate high-frequency waves, or that the amplifier 174 malfunctions, outputting a voltage of 0 V despite of the continued heating of the part. In this case, the moment the temperature represented by the output voltage of the amplifier 174 falls below the first minimum temperature (1), the window comparator 180 supplies a low-level logic signal to the control section 181. The control section 181 therefore supplies a low-level drive signal to the high-frequency wave generator 158. The generator 158 supplies no high-frequency waves to the applicator 171. The treatment on the affected part is thereby terminated.

When the dial 175 V of the target-temperature setting section 175, thus setting the target temperature of 43° C., the automatic maximum-temperature setting section 177 sets a temperature which is 2° C. higher than the target temperature.

Prior to the start of the heating of the part, the automatic minimum-temperature setting section 178 sets the second minimum temperature of 30° C., which is far below the target temperature (43° C.). When the section 178 receives a signal from the timer 179 upon lapse of one minute from the start of the heating, it sets the first minimum temperature of 40° C., which is only 3° C. lower than the target temperature (43° C.). The reason why so will be described below.

Neither the maximum temperature nor the minimum temperature must be close to the target temperature. Otherwise, the temperature-measuring system or the heating system will be considered malfunctioning even if the temperature of the part undergoes normal changes. Before heated, the affected part may have a temperature far below the target temperature. Hence, the maximum temperature temperature is set at 45° C., whereas the minimum temperature is set at 30° C. at the start of the heating and increased to 40° C. upon lapse of one minutes from the start of the heating.

In the case where cooling water is circulated in the applicator 171, the temperature which the part has at the start of heating is lower than the patient's temperature. Therefore, the automatic minimum-temperature setting section 178 may set the minimum temperature at, for example, 0° C. at the start of heating and at 30° C. one minute after the start of heating.

As described above, whether the thermocouple 172, the high-frequency wave generator 158 or the amplifier 174 is malfunctioning or not can be determined by comparing the output voltage of the amplifier 174 (i.e., the temperature of the part) with the output voltage of the section 177 (i.e., the maximum temperature) and with the output voltage of the section 178 (i.e., the minimum temperature). This ensures a safe heating of the affected part. In addition, since the minimum temperature is automatically increased upon lapse of a predetermined time from the start of heating, the affected part can be reliably heated, even if the part has a relatively low temperature when the heating is started.

Figure 36:
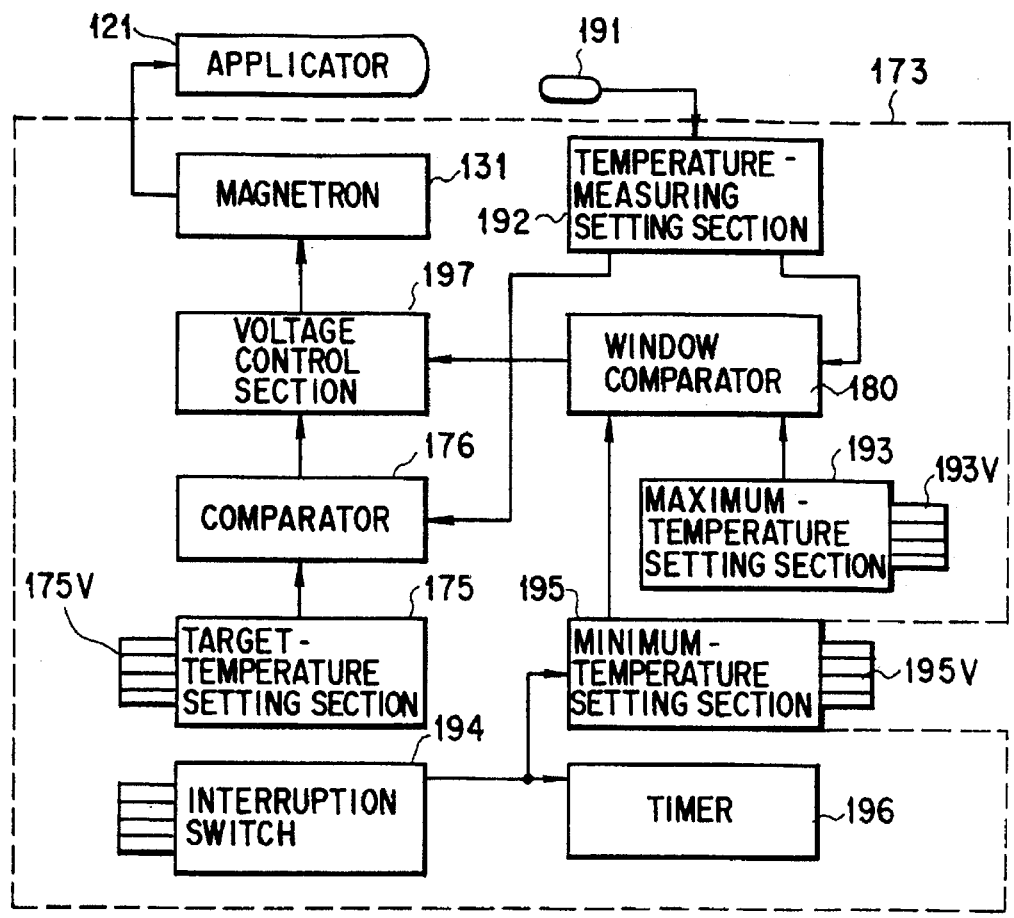
FIG. 36 is a block diagram illustrating a hyperthermia device which is a twelfth embodiment of this invention.
Figure 37:
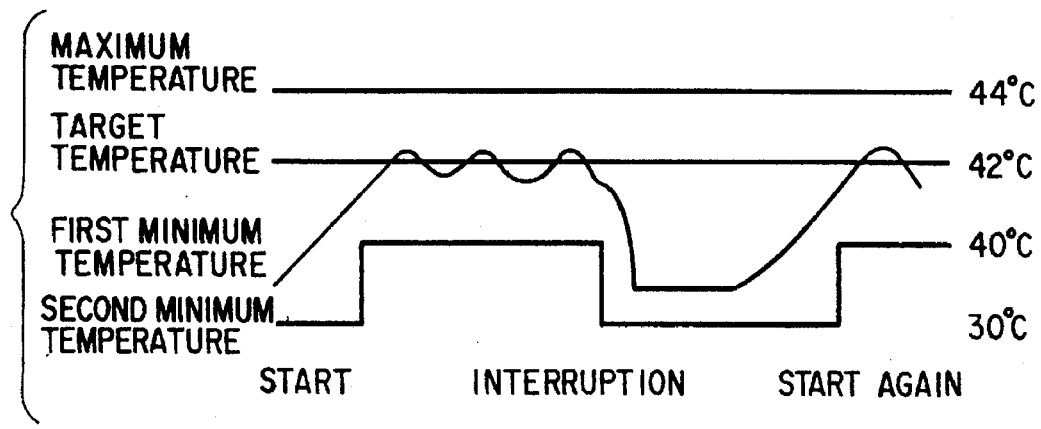
FIG. 37 is a timing chart indicating how the temperature of an affected part changes as the part receives treatment performed by means of the hyperthermia device shown in FIG. 36.

Another hyperthermia device, which is the twelfth embodiment of this invention, will be described with reference to FIGS. 36 and 37. FIG. 36 is a block diagram, and FIG. 37 is a timing chart showing how the temperature of an affected part changes.

The twelfth embodiment is characterized in two respects. First, the application of high-frequency waves is interrupted when the temperature of an affected part falls within a range. Secondly, as illustrated in FIG. 37, the lower limit of the range, or the minimum temperature, is set at the second value (2) when the heating of the part is started, and at the first value (1) greater than the second value (2), upon lapse of one minute from the start of the heating or the start of any additional heating.

As shown in FIG. 36, the hyperthermia device comprises an applicator 121, an optical-fiber thermometer 191, and a main section 173. The main section 173 contains a magnetron 131, a target-temperature setting section 175, a comparator 176, a window comparator 180, a temperature-measuring section 192, a maximum-temperature setting section 193, an interruption switch 194, a minimum-temperature setting section 195, a timer 196, and a voltage control section 197.

The optical-fiber thermometer 191 is located outside the main section 137, for detecting the temperature of an affected part. Its output is connected to the temperature-measuring section 192. The output of the section 192 is connected one of the two inputs of the comparator 176 and to one of the three inputs of the window comparator 180. The temperature-measuring section 192 has such an amplification factor that its output voltage is 0.1× (temperature of the part) [v]. Thus, if the temperature of the affected part is 40° C., the output voltage of the section 192 will be 4 V (=0.1×40).

The other input of the comparator 176 is connected to the output of the target-temperature setting section 175. The section 175 has a dial 175 V, which is rotated to set a target temperature. The target-temperature setting section 175 is designed to output a voltage which corresponds to one tenth of the target temperature (=0.1× the target temperature [V]). The output of the section 175 is connected to the second input of the comparator 176.

The maximum-temperature setting section 193 has a dial 193 V, which is rotated to set a maximum temperature. The section 193 is designed to output a voltage which corresponds to the maximum temperature set by rotating the dial 193 V. The interruption switch 194 is connected to the maximum-temperature setting section 193 and also to the timer 196. The timer 196 generates a signal upon lapse of a predetermined time, e.g., one minute, from the time the applicator 121 starts applying microwaves to the affected part or from the time the interruption switch 194 is operated.

The minimum-temperature setting section 195 has a dial 195 V, which is rotated to set the first minimum temperature (1) and the second minimum temperature (2). The section 195 is designed to output a signal to the window comparator 180. The output signal of the minimum-temperature setting section 195 is changed in level in accordance with the timing signals supplied from the timer 196. More precisely, as shown in FIG. 37, the output signal of the section 195 remains at a low level for one minute from the start of heating, rises to a high level upon lapse of the one-minute period, and falls to the low level when the heating is interrupted, remains at the low level for one minute thereafter, and rises to the high level upon lapse of this one-minute period. The high and low levels of the signal correspond to the first minimum temperature (1) and the second minimum temperature (2), respectively.

The target temperature is set at 43° C. The maximum temperature, the first minimum temperature (1) and the second minimum temperature (2) are set at 45° C., 40° C. and 30° C., respectively, for the same reason stated above in conjunction with the eleventh embodiment.

The comparator 176 is designed to output a logic signal. The logic signal is at the high level if the temperature of the part is equal to or lower than the target temperature, and at the low level if the temperature of the part is higher than the target temperature. The output of the comparator 176 is connected to one of the two inputs of the voltage control section 197.

The other input of the control section 197 is connected to the output of the window comparator 180. The window comparator 180 is designed to generate a logic signal. The logic signal is at the high level if the temperature of the part falls within a range the lower limit of which is the first or second minimum temperature and the upper limit of which is the maximum temperature, and at the low level if the temperature of the part falls outside that range.

The voltage control section 197 is designed to generate a logic product of the logic signals output from the comparator 176 and the window comparator 180, and to produce a drive signal. The drive signal is at a high level if the logic product is "1" and at a low level if the logic product is "0." The output of the voltage control section 197 is connected to the high-frequency wave generator 158.

The magnetron 131 starts generating microwaves in response to the high-level drive signal, and stops generating microwaves in response to the low-level drive signal. The generator 158 is connected to the applicator 121, which can apply microwaves to the affected part.

The operation of the twelfth embodiment, described above, will now be explained.

At first, the dials 175 V, 193 V and 195 V are rotated, setting the target temperature, the maximum temperature and two minimum temperatures (1) and (2). Then, the magnetron 131 is driven, whereby the applicator 121 starts applying microwaves to the affected part. The signal supplied to the window comparator 180 from the minimum-temperature setting section 195 remains at the low level for one minutes from the start of heating and represents the second minimum temperature (i.e., 30° C.) for this one-minute period.

The comparator 176 compares the temperature of the part, measured by the temperature-measuring section 192, with the target temperature set by operating the target-temperature setting section 175. The comparator 176 supplies a high-level logic signal to the voltage control section 197 if the temperature measured by the section 192 is equal to or lower than the target temperature, and a low-level signal to the section 197 if the temperature measured by the section 192 is higher than the target temperature. The voltage control section 197 generates a high-level drive signal upon receipt of the high-level logic signal, and a low-level drive signal upon receipt of the low-level logic signal. The magnetron 131 starts generating microwaves in response to the high-level drive signal, and stops generating microwaves in response to the low-level drive signal.

The temperature of the affected part is thereby controlled to become equal to the target temperature set by operating the target-temperature setting section 175.

Before the application of microwaves, the affected part has a temperature nearly equal to 36° C., i.e., the patient's temperature. Some time after the application of microwaves has been started, the temperature of the part repeatedly rises above and falls below the target temperature, as illustrated in FIG. 37. This is because the section 197 outputs a high-level signal to the magnetron 131 every time the temperature of the part falls below the target temperature, and the section 197 outputs a low-level signal to the magnetron 131 every time the temperature of the part rises above the target temperature.

Should the heating of the affected part be continued by some cause even after the temperature of the part has risen above the target temperature, the parts adjacent to the affected part would be heated excessively. In this case, when the temperature measured by the temperature-measuring section 192 rises above the maximum temperature, the window comparator 180 supplies a low-level logic signal to the voltage control section 197. Responding to the low-level logic signal, the section 197 supplies a low-level drive signal to the magnetron 131. The magnetron 131 stops supplying microwaves to the applicator 121, whereby the temperature of the part starts falling.

Should the temperature measured by the temperature-measuring section 192 fall below the first minimum temperature (1), it is determined that the magnetron 131 malfunctions, failing to generate microwaves at all. In this case, the moment the temperature measured by the temperature-measuring section 192 falls below the first minimum temperature (1), the window comparator 180 supplies a low-level logic signal to the voltage control section 197. The section 197 therefore supplies a low-level drive signal to the magnetron 131. The magnetron 131 supplies no microwaves to the applicator 121. The treatment on the affected part is thereby terminated.

The interruption switch 194 is pushed, thereby interrupting the heating of the part, if necessary for some reason. During the interruption of the heating, the part is cooled to a temperature similar to the patient's temperature. At the time the switch 194 is pushed, not only stopping the heating, but also clearing the timer 196, a signal is supplied to the the minimum-temperature setting section 195. The minimum temperature is thereby decreased from the first value (1) to the second value (2). Upon lapse of one minute from the start of the second heating, the minimum temperature is increased from the second value (2) to the first value (1).

In the twelfth embodiment, a broad temperature range can be set, not only at the time the heating is started, but also at the time the heating is interrupted. This ensures a safe heating of the affected part.

A hyperthermia device, which is the thirteenth embodiment of the present invention, will be described with reference to FIGS. 38 to 41. FIG. 38 is a block diagram; FIG. 39 is a timing chart showing how the maximum and minimum temperature are changed; FIG. 40 is also a timing chart illustrating how the maximum and minimum temperature are changed; and FIG. 41 is a timing chart showing how the minimum temperature is changed.

In the eleventh embodiment (FIG. 34), the maximum-temperature setting section 177 and the minimum-temperature setting section 178 set the maximum temperature and the minimum temperature, respectively, in accordance with the target temperature set by operating the target-temperature setting section 175. The thirteenth embodiment is characterized in that an automatic maximum/minimum temperature setting section 203 automatically sets both the maximum temperature and the minimum temperature in accordance with the data which supplied from a computer 202 and which represents the shape of an affected part and that of an applicator.

The thirteenth embodiment has two applicators 151a and 151b which are to be located, opposing each other, in the body cavity in which the affected part is present. A thermocouple 152b is mounted on the second applicator 151b, for detecting the temperature of the affected part.

Those components of the thirteenth embodiment, which are identical or similar to those of the eleventh embodiment (FIG. 34), are designated at the same reference numerals in FIG. 38 and will not be explained in detail in the following description.

As shown in FIG. 38, the thirteenth embodiment comprises a main section 173, a keyboard 201, and a cooling device 204. The keyboard 201 and the cooling device 204 are provided outside the main section. So are the applicators 151a and 151b.

The keyboard 201 is connected to the computer 202 which is located outside the main section 173. The keyboard is operated to input to the computer various parameters required for controlling the heating of the affected part. Among these parameters are: the shape of the applicators and the shape of the part (e.g., the lower limb, upper limb, the trunk, the stomach, the liver, the esophagus, or the rectum). The shapes of the applicators and that of the affected part may be classified as "circular," "rectangular," "cylindrical" or "tubular." The keyboard 201 is connected to the computer 202.

The computer 202 outputs control signals representing the parameters input by operating the keyboard 201. These control signals are supplied to the automatic maximum/minimum temperature setting section 203 which is incorporated in the main section 173. The section 203 sets a maximum temperature and a minimum temperature in accordance with the control signals as shown in FIG. 41, and outputs voltages corresponding to these temperature. The output voltages of the section 203 are input to the window comparator 180. As illustrated in FIG. 41, the minimum temperature is increased stepwise upon lapse of X minutes from the start of heating, as in the eleventh embodiment (FIGS. 34 and 35).

The cooling device 204 comprises a cooling water pump 205, a cooling unit 206 and a cooling water tank 207. The pump 205 is connected to the applicators 151a and 151b, for supplying cooling water from the tank 207 into the applicators, and from the applicators back into the tank 207. The cooling unit 206 is located between the pump 205 and the tank 207 and connected thereto, for cooling the water.

The operation of the thirteenth embodiment will be explained below.

Before heating the affected part, the keyboard 201 is operated, thereby inputting the heating parameters (e.g., the shape of the applicator and the shape of the affected part) to the computer 202. The computer 202 supplies control signals corresponding to these parameters, to the automatic maximum/minimum temperature setting section 203. In accordance with the control signals, the section 203 sets the maximum and minimum temperatures at such values as shown in FIG. 41. The section 203 outputs the voltages corresponding to these temperatures, to the window comparator 180. Thereafter, the thirteenth embodiment operates in the same way as the eleventh embodiment (FIG. 34).

With the thirteenth embodiment it is possible to vary the maximum and minimum temperatures in two alternative ways. In the first alternative way, the maximum temperature and the minimum temperature are changed symmetrically with respect to the time axis, as illustrated in FIG. 40. In the second alternative way, both the maximum temperature and the minimum temperature are simultaneously decreased and then simultaneously increased as shown in FIG. 40. In either alternative way, the temperatures are changed upon lapse of 30 seconds from the start of heating.

In the thirteenth embodiment, the maximum and minimum temperature are automatically changed in accordance with the shape of the affected part being treated and also the shape of the applicators 151a and 151b. Therefore, with the embodiment it is possible to treat the affected part in high safety.

Still another hyperthermia device, which is a fourteenth embodiment of the invention, will described with reference to FIGS. 42 and 43. FIG. 42 is a block diagram, and FIG. 43 is a circuit diagram showing the target-temperature setting section incorporated in the device.

As shown in FIG. 42, the hyperthermia device comprises a main section 3, an applicator 121 and a thermocouple 122. The main section 3 contains a thermocouple amplifier 124, a magnetron 131, a voltage control section 147, a target-temperature setting section, a comparator 176, and a timer 211.

The applicator 121 is inserted into a body cavity, for applying microwaves to an affected part present in the body cavity. The thermocouple 122 is mounted on the applicator 121, for detecting the temperature of the affected part.

The output voltage of the thermocouple 121, which represents the temperature of the part, is input to the thermocouple amplifier 124, which amplifies the voltage. The amplifier 124 has such an amplification factor that its output voltage is 0.1× (temperature of the part) [V]. Thus, if the temperature of the affected part is 40° C., the output voltage of the amplifier 125 will be 4 V (=0.1×40). The output voltage of the amplifier 124 is input to one of the two inputs of the comparator 176. Input to the other input of the comparator 176 is the output voltage of the target-temperature setting section 175.

The comparator 176 supplies a high-level logic signal to the voltage control section 147 if the temperature measured by the thermocouple 122 is equal to or lower than the target temperature, and a low-level signal to the section 147 if the temperature measured by the thermocouple 122 is higher than the target temperature. Connected to the voltage control section 147 is the timer 211 which starts measuring time at the start of heating. The voltage control section 147 generates a high-level drive signal upon receipt of the high-level logic signal, and a low-level drive signal upon receipt of the low-level logic signal. The drive signal is supplied to the magnetron 131. The magnetron 131 starts generating microwaves in response to the high-level drive signal, and stops generating microwaves in response to the low-level drive signal. The voltage control section 147 produces a chip-selecting signal CS and supplies it to the target-temperature setting section 175.

The target-temperature setting section 175 will be described in more detail, with reference to FIG. 43.

As shown in FIG. 43, the section 175 comprises a variable resistor IC 212, an UP button 213, a DN button 214 and two resistors R and R'. The resistor IC 212 and the resistors R and R' are connected, constituting a series circuit which is connected between the power supply Vcc and the ground GND. The UP button 213 and the DN button 214 are connected two of the input pins of the resistor IC 212, respectively. When the UP button 214 is operated, the resistance of the resistor IC 212 will be increased, and the output voltage of the IC 212 will increase. When the DN button 214 is operated, the resistance of the IC 212 will be decreased, and the output voltage of the IC 212 will decrease. The output voltage of the resistor IC 212, which corresponds to the target temperature, is output from the terminal a of the resistor IC 212 to the comparator 176.

The fourteenth embodiment controls the temperature of the affected part, exactly in the same way as the twelfth embodiment (FIG. 36). While the section 147 is supplying a drive signal to the magnetron 131, thereby controlling the temperature of the affected part, the chip-selecting signal CS output by the voltage control section 147 remains at a high level. The signal CS is inverted before it is input to the resistor IC 212. Hence, the resistance of the IC 212 cannot be changed while the voltage control section 147 is driving the magnetron 131.

As described above, in the fourteenth embodiment of the invention, the target temperature cannot be changed by means of hardware while the voltage control section 147 is driving the magnetron 131, thereby heating the affected part. Therefore, it is impossible to set the target temperature at an excessively high value during the heating of the part, whereby the part is prevented from being heated excessively. This ensures a safe treatment of the affected part.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An electromagnetic thermatological device comprising a main body coupled to an applicator, the applicator being insertable into a urethra of a body, and wherein:

said applicator comprises:
   a distal end and a proximal end;
   a wave-applying section provided at the distal end, for applying electromagnetic waves to an affected body part;
   a first temperature sensor mounted on a surface of the distal end of the applicator, for detecting a first temperature of the affected body part;
   a second temperature sensor provided at the distal end of the applicator and spaced apart from said first temperature sensor along an axis of the applicator, for detecting a second temperature of a body part other than the affected body part;
   a power supply line mounted on the proximal end of the applicator and connected at one end to said wave-applying section; and
   a signal line mounted on the proximal end of the applicator, for transmitting signals representing the first and second temperature, and said main body comprises:
   means for setting a target temperature for achieving a thermatological treatment;
   means for setting a protect temperature for protecting an unaffected body part from the thermatological treatment;
   a wave-generating section for generating electromagnetic waves and for supplying electromagnetic waves to the wave-applying section of the applicator;
   means for comparing the first temperature with the target temperature and controlling emission of waves from said wave-generating section in accordance with a difference between the compared first temperature and target temperature; and
   means for comparing the second temperature with the protect temperature and stopping or reducing the emission of waves of said wave-generating section when the second temperature falls below the protect temperature.

2. The device according to claim 1, wherein said first temperature sensor is adapted to detect a temperature of a urethral mucosa of a prostate, and said second temperature sensor is adapted to detect a temperature of a urethral sphincter muscle.

3. The device according to claim 1, which further comprises:
   a third temperature sensor to be inserted into a body cavity other than the body cavity into which said applicator is to be inserted;
   means for connecting the third temperature sensor to said main body; and means for setting a second protect temperature, and wherein the temperature detected by said third temperature sensor is compared with the second protect temperature, and said wave-generating section is arranged to stop or reduce emission of waves when the temperature detected by said third temperature sensor is higher than the second protect temperature.

4. The device according to claim 1, wherein the target temperature and the protect temperature are independently settable.

5. The device according to claim 1, wherein the protect temperature is automatically set in accordance with the target temperature.

6. The device according to claim 1, wherein the protect temperature changes with time, from a start of a heating operation.

7. The device according to claim 1, further comprising:

means for comparing the first temperature detected at a start of a heating operation or at a start of another heating operation after interruption of a prior heating operation, with a second temperature detected during the heating operation or during the another heating operation, and for causing said wave-generating section to stop or reduce emission of waves when the first temperature is equal to or less than the second temperature.

8. The device according to claim 1, further comprising:

means for setting a maximum temperature higher than the target temperature and a minimum temperature lower than the target value, and for causing said wave-generating section to stop or reduce emission of waves when the first temperature rises above the maximum temperature or falls below the minimum temperature after the start of a heating operation.

9. The device according to claim 1, wherein said target temperature is set to be about 39° C., and said protect temperature is about 45° C.

* * * * *

UNITED STATES PATENT AND TRADEMARK OFFICE
CERTIFICATE OF CORRECTION

PATENT NO. : 5,628,771
DATED : May 13, 1997
INVENTOR(S) : MIZUKAWA et al.

It is certified that error appears in the above-identified patent and that said Letters Patent is hereby corrected as shown below:

Tilte page, Item [57] ABSTRACT, line 8, delete ", the".

Signed and Sealed this

Third Day of March, 1998

Attest:

BRUCE LEHMAN

Attesting Officer

Commissioner of Patents and Trademarks